United States Patent
Kano et al.

(10) Patent No.: US 10,674,909 B2
(45) Date of Patent: Jun. 9, 2020

(54) OPHTHALMIC ANALYSIS APPARATUS AND OPHTHALMIC ANALYSIS METHOD

(71) Applicant: NIDEK CO., LTD., Gamagori, Aichi (JP)

(72) Inventors: Tetsuya Kano, Aichi (JP); Norimasa Satake, Aichi (JP); Yukihiro Higuchi, Aichi (JP); Yasuhiro Furuuchi, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 173 days.

(21) Appl. No.: 15/696,855

(22) Filed: Sep. 6, 2017

(65) Prior Publication Data

US 2018/0064336 A1    Mar. 8, 2018

(30) Foreign Application Priority Data

Sep. 7, 2016   (JP) .................................. 2016-175039

(51) Int. Cl.
  *G06K 9/00*     (2006.01)
  *A61B 3/12*     (2006.01)
  (Continued)

(52) U.S. Cl.
  CPC .......... *A61B 3/1241* (2013.01); *A61B 3/0025* (2013.01); *A61B 3/102* (2013.01);
  (Continued)

(58) Field of Classification Search
  CPC ..... A61B 3/1241; A61B 3/0025; A61B 3/102; A61B 3/0058; A61B 3/1233; A61B 3/13; A61B 3/14; A61B 5/0066; A61B 5/7203; A61B 5/0073; A61B 5/7445; A61B 5/748; G06T 7/11; G06T 7/0016; G06T 7/0012; G06T 7/73; G06T 7/215; G06T 3/0068; G06T 5/50; G06T 11/003; G06T 11/005;
  (Continued)

(56) References Cited

U.S. PATENT DOCUMENTS 10,398,302 B2 *   9/2019   Meyer .................. A61B 3/0025
10,402,965 B1 *   9/2019   Bagherinia .......... G06T 7/0081
(Continued)

FOREIGN PATENT DOCUMENTS

JP       4-336677 A      11/1992
JP       2012-75938 A     4/2012
(Continued)

OTHER PUBLICATIONS

Communication dated Jan. 28, 2020 issued by the Japanese Intellectual Property Office in counterpart Japanese Application No. 2016-175039.

*Primary Examiner* — Jose L Couso
(74) *Attorney, Agent, or Firm* — Sughrue Mion, PLLC

(57) ABSTRACT

An ophthalmic analysis apparatus for analyzing OCT motion contrast (MC) image data of a subject's eye acquired using an OCT apparatus for ophthalmology includes analysis process means for analyzing the OCT MC image data, in which the analysis process means generates OCT blood vessel change data including temporal change information in relation to a blood vessel region of the subject's eye based on first OCT MC image data and second OCT MC image data acquired at mutually different times.

14 Claims, 8 Drawing Sheets

(51) Int. Cl.
*G06T 7/11* (2017.01)
*A61B 3/00* (2006.01)
*A61B 3/10* (2006.01)
*G06T 3/00* (2006.01)
*G06T 5/50* (2006.01)
*G06T 7/00* (2017.01)
*G06T 15/04* (2011.01)

(52) U.S. Cl.
CPC .............. *G06T 3/0068* (2013.01); *G06T 5/50* (2013.01); *G06T 7/0016* (2013.01); *G06T 7/11* (2017.01); *G06T 15/04* (2013.01); *G06T 2207/10016* (2013.01); *G06T 2207/10028* (2013.01); *G06T 2207/10101* (2013.01); *G06T 2207/30041* (2013.01); *G06T 2207/30101* (2013.01)

(58) Field of Classification Search
CPC ..... G06T 11/006; G06T 11/008; G06T 15/04; G06T 2207/10016; G06T 2207/10028; G06T 2207/10072–10101; G06T 2207/30041; G06T 2207/30101; G06T 2207/30104; G06T 2210/41; G06T 2211/40; G01B 9/02087; G01B 9/02091; G01B 9/0201; G01B 9/02045; G01B 9/02044; G01B 9/02083; G01B 9/02089; G06K 9/0061; G06K 9/6289; G06K 9/00496; G06K 2209/05; G06F 19/321; Y10S 5141/912

See application file for complete search history.

(56) References Cited

U.S. PATENT DOCUMENTS

| | | | |
|---|---|---|---|
| 10,420,461 B2* | 9/2019 | Oishi | A61B 3/102 |
| 10,492,682 B2* | 12/2019 | Shiba | A61B 3/0058 |
| 2008/0025570 A1* | 1/2008 | Fingler | A61B 3/102 |
| | | | 382/107 |
| 2014/0112562 A1 | 4/2014 | Yamakawa et al. | |
| 2014/0221827 A1* | 8/2014 | Motaghiannezam | |
| | | | G01N 21/4795 |
| | | | 600/425 |
| 2015/0002813 A1 | 1/2015 | Ota et al. | |
| 2015/0168127 A1 | 6/2015 | Takeno et al. | |
| 2016/0183786 A1 | 6/2016 | Wei et al. | |
| 2016/0198939 A1 | 7/2016 | Fukuhara et al. | |
| 2016/0317016 A1* | 11/2016 | Oishi | A61B 3/102 |
| 2017/0065170 A1* | 3/2017 | Yamashita | A61B 3/102 |
| 2019/0380588 A1* | 12/2019 | Takeno | G01N 21/17 |

FOREIGN PATENT DOCUMENTS

| | | |
|---|---|---|
| JP | 2014-83266 A | 5/2014 |
| JP | 2015-29558 A | 2/2015 |
| JP | 2015-131107 A | 7/2015 |
| WO | 2014/207904 A1 | 12/2014 |

* cited by examiner

FIRST MC IMAGE DATA − SECOND MC IMAGE DATA = DIFFERENCE DATA

FIRST MC IMAGE DATA − SECOND MC IMAGE DATA = DIFFERENCE DATA

FIRST MC IMAGE DATA   SECOND MC IMAGE DATA   DIFFERENCE DATA

OPHTHALMIC ANALYSIS APPARATUS AND OPHTHALMIC ANALYSIS METHOD

BACKGROUND

The present disclosure relates to an ophthalmic analysis apparatus and an ophthalmic analysis method for analyzing data of a subject's eye including blood vessel information of the subject's eye.

BACKGROUND ART

Recently, an apparatus for obtaining OCT motion contrast image data (hereinafter, MC image data) by applying an optical coherence tomography (OCT) technology has been proposed (for example, refer to JP-A-2015-131107).

SUMMARY

Meanwhile, in a case in which a follow-up analysis is performed using the MC image data, for example, a method of obtaining an analysis value such as a blood vessel density by analyzing each MC image data acquired at different times through an image process is considered. However, with the method alone, the analysis values can only be compared as numerical values, and it is difficult to confirm temporal change.

This disclosure has been made in consideration of the problems described above, and is for providing an ophthalmic analysis apparatus and an ophthalmic analysis method which appropriately recognizes temporal changes in an OCT motion contrast image.

In order to solve the above-described problems, the disclosure is characterized by having configurations below:

An ophthalmic analysis method comprising:

acquiring first OCT MC (motion contrast) image data of a subject's eye and second OCT MC image data of the subject's eye using at least one OCT apparatus for ophthalmology, the first OCT MC image data and the second OCT MC image data being acquired at different times;

analyzing the acquired first OCT MC image data and second OCT MC image data to generate OCT blood vessel change data including temporal change information in relation to a blood vessel region of the subject's eye based on the first OCT MC image data and the second OCT MC image data.

An ophthalmic analysis apparatus comprising:

a processor; and memory storing computer readable program, when executed by the processor, causing the ophthalmic analysis apparatus to execute:

acquiring first OCT MC (motion contrast) image data of a subject's eye and second OCT MC image data of the subject's eye using at least one OCT apparatus for ophthalmology, the first OCT MC image data and the second OCT MC image data being acquired at different times;

analyzing the acquired first OCT MC image data and second OCT MC image data to generate OCT blood vessel change data including temporal change information in relation to a blood vessel region of the subject's eye based on the first OCT MC image data and the second OCT MC image data.

A non-transitory computer readable recording medium storing a computer readable program, when executed by a processor of an ophthalmic analysis apparatus, causing the ophthalmic analysis apparatus to execute:

acquiring first OCT MC (motion contrast) image data of a subject's eye and second OCT MC image data of the subject's eye using at least one OCT apparatus for ophthalmology, the first OCT MC image data and the second OCT MC image data being acquired at different times;

analyzing the acquired first OCT MC image data and second OCT MC image data to generate OCT blood vessel change data including temporal change information in relation to a blood vessel region of the subject's eye based on the first OCT MC image data and the second OCT MC image data.

DESCRIPTION OF ILLUSTRATIVE EMBODIMENTS

Figure 1:
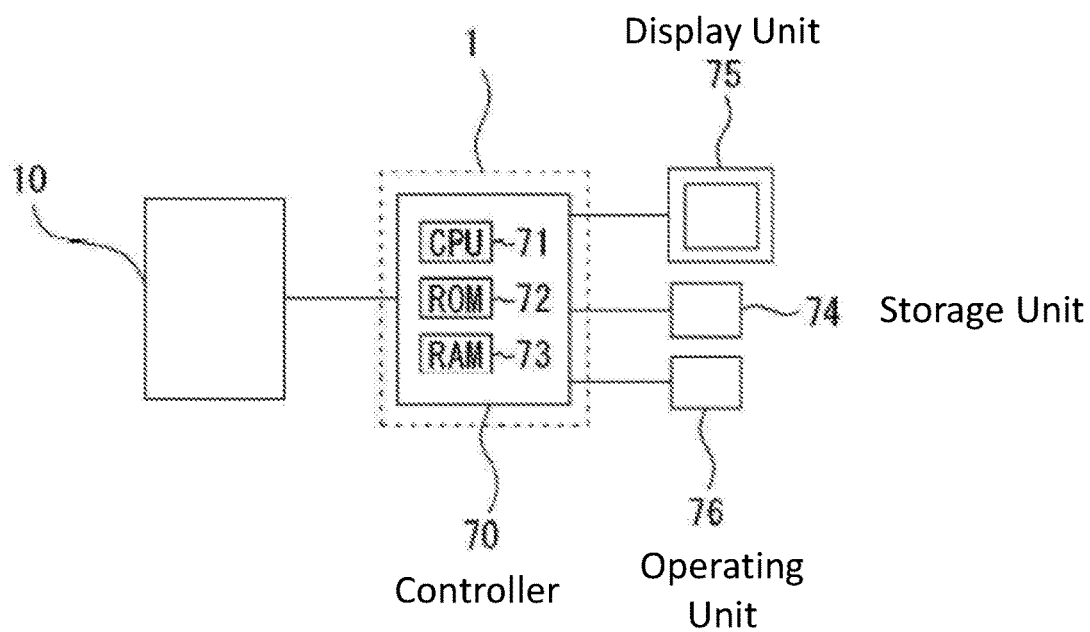
FIG. 1 is a block diagram illustrating an outline of an example.

Hereinafter, exemplary embodiments in this disclosure will be described.

<Outline>

An ophthalmic analysis apparatus may be used for analyzing OCT motion contrast image data (hereinafter, MC image data) of a subject's eye which is acquired by an OCT apparatus for ophthalmology (for example, refer to FIGS. 1 and 2). The ophthalmic analysis apparatus may be provided with an analysis processing unit for performing an analysis process on the MC image data. Further, the ophthalmic analysis apparatus may be an apparatus integrated with an apparatus main body of the OCT apparatus for ophthalmology, or may be an apparatus separately provided from the apparatus main body of the OCT apparatus for ophthalmology. As the ophthalmic analysis apparatus, a general purposed personal computer may be used. In addition, as the analysis processing unit, for example, a processor such as a CPU may be used.

The MC image data may be acquired when OCT data of a subject's eye which is detected by the OCT apparatus for ophthalmology is processed. In this case, for example, the MC image data may be acquired when at least two OCT signals at different times in relation to the same position are processed (for example, refer to FIGS. 3A to 3C). Here, the MC image data may be, for example, image data in which movement of blood flow is imaged based on the OCT data, and in this case, the MC image data may be image data in which the movement of the blood flow is represented by luminance values. In addition, the MC image data may be image data in which a blood vessel region is imaged based on the OCT data, and in this case, may be image data in which the blood vessel region is represented by the luminance values. The MC image data of the subject's eye may be, for example, MC image data of a fundus, or may be MC image data of an anterior eye part.

The MC image data may be B scan MC image data in which the motion contrast data (hereinafter, MC data) at different positions are arranged. In addition, the MC image data may be three-dimensional MC image data in which the MC data is arranged within a two-dimensional range in a direction orthogonal to a depth direction.

The MC image data may be front MC image data (en-face MC image data) based on the three-dimensional MC image data, for example, may be front MC image data based on the entirety of the depth direction of the three-dimensional MC image data, or may be front MC image data based on a part of the depth direction of the three-dimensional MC image data. As a calculating method, an integration process of luminance values in the depth direction may be used, or other methods (for example, histogram calculation and maximum value extraction) may be used.

The analysis processing unit may acquire, for example, at least one of the analysis results by performing an analysis process with respect to the MC image data. The analysis processing unit may analyze, for example, at least two MC image data items of the subject's eye acquired at mutually different times, and may acquire the analysis result.

At least the two MC image data items acquired at different times may include, for example, at least first MC image data and second MC image data. The second MC image data may be second MC image data acquired later than the first MC image data, or may be second MC image data acquired before the first MC image data.

In order to perform a follow-up, at least the two MC image data items acquired at different times may be, for example, the MC image data items relating to the same part of the same eye (for example, fundus or anterior eye), which is acquired at the same position. In this case, for example, the MC image data may be MC image data in the same scanning region, or may be MC image data of the same attention part (for example, macula, optic nerve head, or sclera).

At least the two MC image data items acquired at different times may be MC image data based on OCT data obtained by the same OCT apparatus for ophthalmology, or may be MC image data based on OCT data obtained by different OCT apparatuses for ophthalmology.

In the ophthalmic analysis apparatus, for example, a storage unit may be provided, the storage unit may store at least the two MC image data items acquired at mutually different times, and the analysis processing unit may analyze at least the two MC image data items stored in the storage unit in advance and acquire an analysis result.

<Generation of OCT Blood Vessel Change Data>

The analysis processing unit may generate, for example, the OCT blood vessel change data including the temporal change information in relation to the blood vessel region, based on the first MC image data and the second MC image data of the same subject's eye acquired at mutually different times (for example, refer to FIGS. 4 to 18). In this case, the analysis processing unit may compare, for example, the first MC image data and the second MC image data, and may generate the OCT blood vessel change data including the temporal change information of the MC image data in relation to the blood vessel region based on the compared result.

The OCT blood vessel change data may be generated based on B scan MC image data acquired at mutually different times, may be generated based on the three-dimensional MC image data acquired at mutually different times, and may be generated based on the front MC image data acquired at mutually different times.

The OCT blood vessel change data may be, for example, the blood vessel change data including the temporal change information in relation to the blood vessel region in accordance with an acquiring position (for example, in each pixel or in each section) of the subject's eye. The OCT blood vessel change data may be, for example, blood vessel change data in which the temporal change information in relation to the blood vessel region is imaged.

The analysis processing unit may output, for example, the generated OCT blood vessel change data, and may store the data in the storage unit. In order to output the data, a display unit may be used, a printer may be used, or the data may be transferred to an external server. Hereinafter, in a case in which the OCT blood vessel change data is output to the display unit, as long as the data can be configured to be output, this exemplary embodiment can be applied even when the data is output through another output unit.

For example, when a follow-up analysis is performed by the MC image data using OCT, since a burden on an examinee at the time of being medical-examined by a doctor can be further reduced than a case in which contrast media is used, information useful for diagnosis related to blood vessels can be obtained while reducing the burden on the examinee. In addition, when compared to a case in which numerical values of the analysis values based on an image process of each MC image data are compared, the temporal changes between the MC image data items can be appropriately recognized.

As a case in which the MC image data items are acquired at mutually different times, for example, MC images may be acquired on mutually different examination dates, and accordingly, for example, the temporal change information may be acquired in the long term. In addition, even when an acquiring timing on the same examination date is different (for example, after a certain time has elapsed since previous MC image data has been acquired), and accordingly, for example, the temporal change information in a short period of time (for example, during surgery, before and after surgery, or the like) may be acquired. In this case, for example, the acquiring timing of the MC image may be differed by minute unit or time (hours) unit.

The OCT blood vessel change data including the temporal change information in relation to the blood vessel region may be, for example, the blood vessel change data including the temporal change information in relation to any one of a blood vessel and a blood vessel knob. In addition, the OCT blood vessel change data including the temporal change information in relation to the blood vessel region may be, for example, OCT blood vessel change data including temporal change information in relation to a non-blood vessel region (for example, ischemic region).

The OCT blood vessel change data does not necessarily need to be image data for being output to the display unit or the like.

<Detection Difference of Luminance of First MC Image Data and Second MC Image Data>

The analysis processing unit may generate, for example, the OCT blood vessel change data based on differences of luminance of the first MC image data and the second MC image data acquired at mutually different times (for example, refer to FIGS. 7 to 10). The differences of luminance may be acquired, for example, in accordance with acquiring positions on the subject's eye (for example, in each pixel or in each section).

In this case, the analysis processing unit may generate, for example, difference image data between the first MC image data and the second MC image data. In this case, for example, the analysis processing unit may generate the difference image data in which a difference of luminance is set to a pixel value in the first MC image data and the second MC image data. In a case in which the difference image data is obtained, for example, difference image data in which the difference of luminance is calculated in each pixel may be generated. In addition, difference image data in which the difference of the luminance values in a group of adjacent pixels set as one region is calculated may be generated. In this case, a representative value based on each group of the adjacent pixels is calculated, and the difference image data in which a difference of the representative values is set to a pixel value may be generated.

In a case in which the difference image data is generated, for example, the analysis processing unit may generate the difference image data between raw MC image data items, and the difference image data may be generated after an image process (for example, binarization process) is performed on the OCTMC image data.

The analysis processing unit may obtain, for example, the difference of the luminance values by subtracting a luminance value of MC image data (another of first MC image data and second MC image data), which is set as a reference image, from a luminance value of MC image data (one of first MC image data and second MC image data), which is set as a standard image, in each pixel. As the difference image data, for example, the difference of luminance may be obtained using a ratio of the luminance value in each pixel between the MC image data items.

The analysis processing unit may obtain, for example, binarization image data in relation to presence and absence of the blood vessel in each pixel by respectively performing the binarization process on the first MC image data and the second MC image data, using a threshold for determining the presence and absence of the blood vessel in each pixel. The analysis processing unit may acquire the difference image data in which the difference of the luminance values in each pixel of each binarization image data is set to the pixel value.

The difference image data may include a plus difference and a minus difference as the difference of the luminance values. For example, in a case in which the first MC image data is set as the standard image, and the second MC image data acquired before the first MC image data is set as the reference image, the temporal change in relation to increase of the blood vessel region, such as vascularization of the blood vessel region (for example, vascularization of blood vessel and blood vessel knob), extension of the blood vessel region (for example, extension of blood vessel), and expansion of the blood vessel region (for example, expansion of diameter of blood vessel or blood vessel knob), is expressed as the plus difference (for example, refer to FIGS. 7 and 8).

Figure 9:
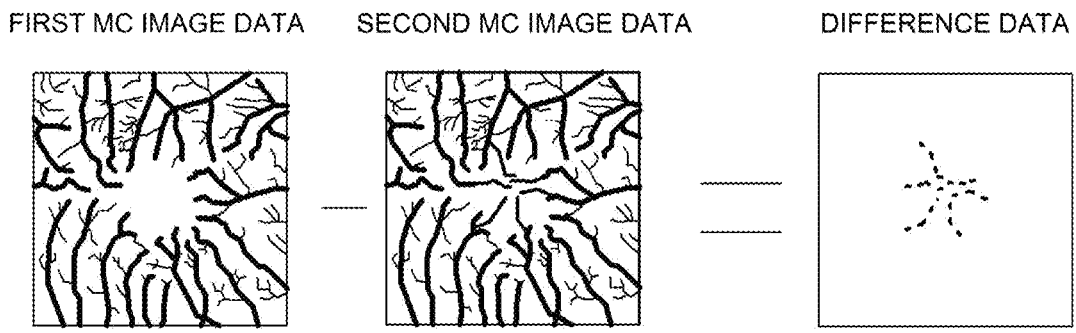
FIG. 9 is a view illustrating an example at the time of obtaining the difference of luminance.
Figure 10:
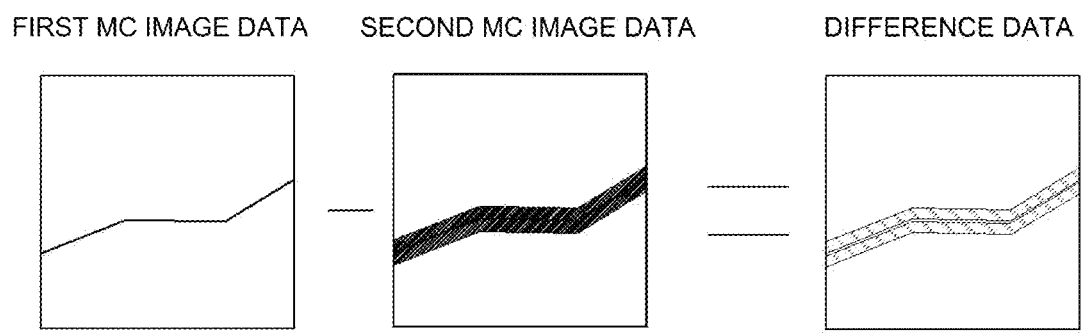
FIG. 10 is a view illustrating an example at the time of obtaining the difference of luminance.

Meanwhile, the temporal change in relation to decrease of the blood vessel region such as extinction (disappearance) of the blood vessel region (for example, extinction (disappearance) of blood vessel and blood vessel knob), shortening of the blood vessel region (for example, shortening of blood vessel), or cutdown of the blood vessel region (for example, cutdown of a diameter of the blood vessel or blood vessel knob), is expressed as a minus difference (for example, refer to FIGS. 9 and 10). In addition, if there is little change, the change is expressed as zero difference. In a case in which the first MC image data is set as a standard image, and the second MC image data acquired later than the first MC image data is set as a reference image, the blood vessel region is expressed as a minus difference. In addition, the decrease of the blood vessel region is expressed as a plus difference.

The MC image data items itself acquired at different times are easily compared by generating the difference image data, the temporal change of the blood vessel region can be directly checked when compared to a case of comparing analysis parameters based on each MC image data, and thereby making it possible to obtain information useful for diagnosis at the time of observing progress.

The difference image data may include difference data depending on the acquiring position of the subject's eye (for example, in each pixel or in each section), and does not necessarily need to be an image type or the like for being output to the display unit or the like. In this case, for example, the difference data is not only luminance values, but also simple numerical values.

The analysis processing unit may remove, for example, noise generated due to unevenness or the like of the luminance value by performing a binarization process on the difference image data. In this case, the binarization process may be performed on the plus luminance value and the minus luminance value. In addition, the analysis processing unit may express a magnitude of the difference of luminance by brightness without performing the binarization process on the difference image data.

The analysis processing unit may apply, for example, the raw difference image data obtained by a difference process between the first MC image data and the second MC image data as the OCT blood vessel change data, and may apply an analyzed image obtained by analyzing the obtained difference image data as the OCT blood vessel change data.

<Position Adjustment Between First MC Image Data and Second MC Image Data>

The analysis processing unit may perform, for example, a position adjusting process between the first MC image data and the second MC image data in at least a depth direction. Further, the analysis processing unit may generate, for example, the OCT blood vessel change data based on the first MC image data and the second MC image data on which the position adjusting process is performed.

As the position adjusting process, the position adjustment is performed on the MC image data itself, the position adjustment is performed between the OCT data items which become basis of the MC image data, and a result thereof may be reflected to the position adjustment between the MC image data items.

In a case in which the position adjusting process is performed, the analysis processing unit may match, for example, the MC image data which is set as the reference image with the MC image data which is set as the standard image by the image process. In a case in which the difference of luminance is obtained, the analysis processing unit may obtain a difference of luminance between the MC image data items in a state of being matched.

The analysis processing unit may perform the position adjustment between B scan MC image data items, or may perform the position adjustment between the three-dimensional MC image data items. In addition, in a case in which the position adjustment is performed between three-dimensional image data items, regarding each B scan MC image data corresponding to a plurality of scan lines forming a three-dimensional image, the position adjustment may be performed among B scan image data items corresponding to the same scan line. In addition, in a case in which the difference of luminance between the front MC image data items is obtained, for example, the analysis processing unit may generate the front MC image data common to a depth region after the position adjustment between images is performed using the three-dimensional MC image data which becomes basis of the front MC image data, three-dimensional OCT image data which becomes basis of the three-dimensional MC image data, or the like, and then may obtain the difference of luminance between two front MC image data items.

For example, when the position adjustment is performed between the MC image data items as described above, for example, regardless of a position deviation between the MC image data items, the temporal change in relation to the blood vessel region can be appropriately recognized.

In a case in which the position adjustment is performed between the image data items, for example, the position deviation may be corrected by A-scan unit for forming the B scan MC image data or the three-dimensional MC image data, or the position deviation in the entire image may be corrected. Of course, a unit of correcting the position deviation is not limited thereto.

The analysis processing unit may correct deviation between the MC image data items in an XY direction by performing the position adjustment in a transverse direction (XY direction) of measuring light in advance, and then may perform the position adjustment in the depth direction, or may perform the position adjustment in the depth direction without performing the position adjustment of the XY direction.

Regarding a specific method of the position adjustment, various image process methods can be used, and thus special description will be omitted. In addition, without being limited to the position adjustment between images, at the time of acquiring the MC image, the position deviation between the images may be reduced in advance by a tracking process of an apparatus.

<Sensitivity Attenuation Correction Between First MC Image Data and Second MC Image Data>

Figure 11:
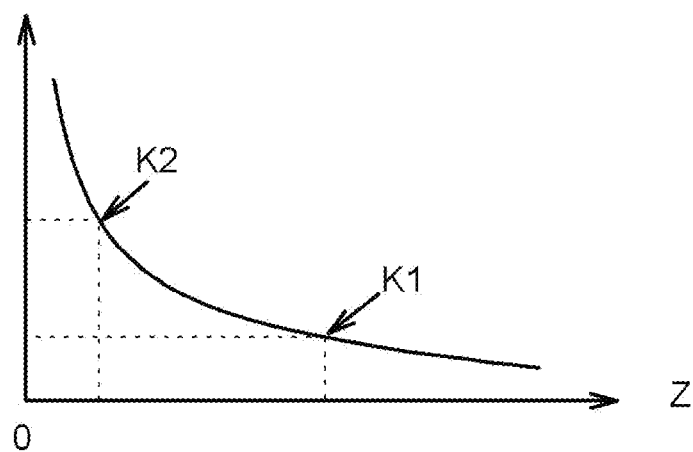
FIG. 11 is a view illustrating an example at the time of performing sensitivity attenuation correction between MC image data items.

The analysis processing unit may correct, for example, a brightness difference between the first OCTMC image data and the second OCTMC image data due to an influence of the sensitivity attenuation in the depth direction (for example, refer to FIG. 11).

In this case, for example, the analysis processing unit may correct change of luminance of the MC image data due to sensitivity attenuation between the MC image data items. In this case, for example, the analysis processing unit may correct the change of luminance of the MC image data due to the sensitivity attenuation in the depth direction in each image in advance, and may obtain the difference of luminance using the MC image data in which the luminance is corrected.

As an example of a case in which luminance change is corrected, the analysis processing unit may perform a normalizing process of the luminance value for correcting the sensitivity attenuation in the depth direction with respect to each MC image data. In this case, for example, the analysis processing unit may adjust the luminance value of the MC image data so that histogram distributions between the MC image data items coincide with each other.

In this case, the analysis processing unit may adjust, for example, the luminance value of the MC image data which is set as the reference image, such that a histogram of the MC image data which is set as the reference image has the same distribution as a histogram of the MC image data which is set as the standard image.

As another method, the analysis processing unit may adjust, for example, the luminance value using a correction table in which a relationship between the depth direction and the sensitivity characteristic is plotted in advance. In this case, the analysis processing unit creates the correction table (for example, refer to FIG. 11) for correcting the change of the luminance value of the MC image data due to the sensitivity attenuation in the depth direction in advance, and may correct the luminance value of the MC image data using the correction table at the time of performing the position adjustment between the images. In this case, the analysis processing unit may obtain, for example, a ratio of a sensitivity characteristic (for example, K1 of FIG. 11) before correcting the position and a sensitivity characteristic (for example, K2 of FIG. 11) after correcting the position at each depth position, and may multiply the ratio by a ratio of the luminance values at each depth position of the MC image data.

In a case in which the position deviation is generated between the MC image data items, there is a possibility that a brightness difference is generated between the MC image data items due to influence (for example, in a case in which OCT data is obtained by SD-OCT) of the sensitivity attenuation in the depth direction. In this case, for example, even when the position deviation between the MC image data items is corrected, there is a possibility that the temporal change in relation to the blood vessel region cannot be appropriately recognized, and the temporal change in the blood vessel region can be accurately recognized by providing a process of correcting the brightness difference, regardless of influence of the sensitivity attenuation.

In addition, there is a possibility that the luminance unevenness is generated in the MC image data due to a status of the subject's eye (for example, eyelashes, blinks, cataract, and the like) at the time of obtaining the MC image data. The analysis processing unit divides, for example, the MC image data into a plurality of regions, and may adjust the luminance value by a divided region unit, such that a representative value (for example, average value or highest frequency value) of the luminance value at each divided region becomes uniform.

<Generation of OCT Blood Vessel Increase-and-Decrease Data>

As the OCT blood vessel change data, the analysis processing unit may generate, for example, the OCT blood vessel increase-and-decrease data including the temporal change information in relation to any one of the increase and the decrease of the blood vessel region, based on the first MC image data and the second MC image data (for example, refer to FIGS. 4 to 10 and FIGS. 16 to 18). The generated OCT blood vessel increase-and-decrease data may be displayed on the display unit, may be stored in the storage unit, or may be transferred to the outside. Accordingly, for example, the temporal change in relation to increase-and-decrease of the blood vessel region can be appropriately recognized.

The increase of the blood vessel region may be, for example, at least any one of the vascularization of the blood vessel region, the extension of the blood vessel region, and the expansion of the blood vessel region. The decrease of the blood vessel region may be, for example, at least any one of the extinction (disappearance) of the blood vessel region, the shortening of the blood vessel region, and the cutdown of the blood vessel region.

In a case in which the OCT blood vessel increase-and-decrease data is generated, for example, the analysis processing unit may obtain the difference of luminance between the first MC image data and the second MC image data, and may generate the OCT blood vessel increase-and-decrease data based on the generated difference of luminance. For example, the analysis processing unit may perform a determination process on the difference of luminance of each pixel, and may generate the OCT blood vessel increase-and-decrease data based on the determined result. In this case, the OCT blood vessel increase-and-decrease data in which the determined result of each pixel is set to the pixel value may be generated.

The analysis processing unit may generate, for example, the difference image data between the first MC image data and the second MC image data, and may generate the OCT blood vessel increase-and-decrease data by performing the determination process on the luminance value of the generated difference image data. In addition, the analysis processing unit may generate, for example, the difference image data itself as the OCT blood vessel increase-and-decrease data.

In a case in which the determination process is performed on the difference of luminance, for example, the analysis processing unit may determine the increase and the decrease of the blood vessel region depending on whether the difference of luminance is positive or negative. For example, in a case in which the first MC image data is set as the standard image, and the second MC image data acquired before the first MC image data is set as the reference image, the analysis processing unit may determine a region having a plus difference of luminance as a region where the blood vessel region is increased, and may determine a region having a minus difference of luminance as a region where the blood vessel region is decreased. In addition, the analysis processing unit may determine a region having zero difference of luminance as a region where the blood vessel region has not been changed (for example, a region where the blood vessel remains, but which is not an original blood vessel). The analysis processing unit may generate the OCT blood vessel increase-and-decrease data using the determined result, and display the data on the display unit.

In a case in which the OCT blood vessel increase-and-decrease data including the temporal change information in relation to both the increase and the decrease of the blood vessel region is generated and displayed on the display unit, for example, based on the first MC image data and the second MC image data, the analysis processing unit may generate the OCT blood vessel increase-and-decrease data including the temporal change information in relation to the increase and the decrease of the blood vessel region, and may display the increase and the decrease of the blood vessel region in different displaying forms at the time of displaying the generated OCT blood vessel increase-and-decrease data on the display unit.

As one of the different displaying forms, for example, the increase and the decrease of the blood vessel region may be displayed in different colors. In this case, for example, a color map may be used of which colors of pixels of the image data are displayed in accordance with the increase and the decrease of the blood vessel region. For example, a region where the blood vessel region is increased may be displayed in red, a region where the blood vessel region is decreased may be displayed in blue, and a region which has not been changed may be displayed as colorless. Of course, the types of colors are not limited thereto. The color map may be used of which the colors varies depending on a magnitude of the difference of luminance may be used. As another of the different displaying forms, for example, at least any one of brightness and contrasting density may be differently displayed depending on the increase and the decrease of the blood vessel region, and may be displayed in different line types. Otherwise, the increase and the decrease may be displayed to be shaded.

Images of first data, which includes the temporal change information in relation to the increase, and second data, which includes the temporal change information in relation to the decrease, may be formed as the same image data, or may be formed as separate image data. In addition, the first data and the second data described above may be displayed on the display unit as one image data in a common display region, may be displayed on the display regions at the same time by being separately divided, or may be displayed to be switched.

In a case in which the OCT blood vessel increase-and-decrease data is generated, for example, the analysis processing unit may generate the OCT blood vessel increase-and-decrease data including the temporal change information in relation to at least any one of the vascularization and the extinction of the blood vessel region. Accordingly, for example, the temporal change in relation to the vascularization and the extinction of the blood vessel region can be appropriately recognized.

In a case in which the temporal change information in relation to the increase of the blood vessel region is obtained, for example, based on the first MC image data and the second MC image data, the analysis processing unit may determine whether or not the increase of the blood vessel region is the vascularization of the blood vessel region, the extension of the blood vessel region, or the expansion of the blood vessel region. In addition, the analysis processing unit may determine only one of the vascularization of the blood vessel region, the extension of the blood vessel region, and the expansion of the blood vessel region.

Figure 12:
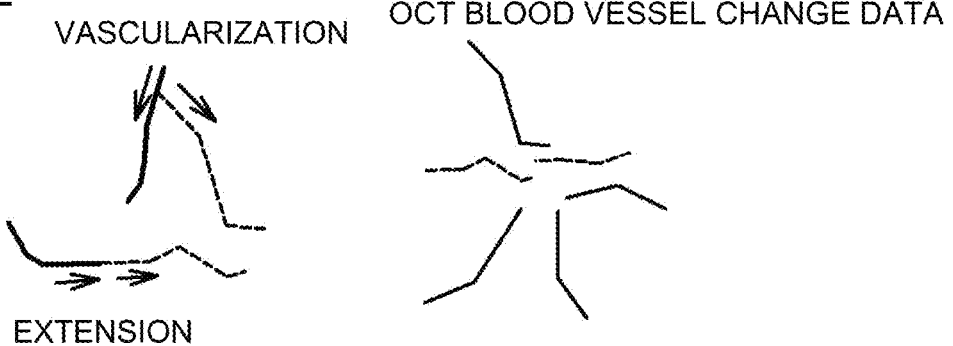
FIG. 12 is a view illustrating an example at the time of determining vascularization and extension of a blood vessel region.

For example, the analysis processing unit may determine the vascularization and the extension of the blood vessel region by collating a part of the increase of the blood vessel region in the MC image data (standard MC image data) which is set as the standard image with the MC image data which is set as the reference image (reference MC image data) (for example, refer to FIG. 12). In this case, collating may be performed in a travelling direction of the blood vessel, and for example, when the travelling direction of the blood vessel corresponding to an increased region (for example, refer to a broken line of a left drawing of FIG. 12) in the standard MC image data is collated with a travelling direction of the blood vessel (for example, refer to a solid line of the left drawing of FIG. 12) in the reference MC image data, if the travelling directions do not coincide with each other, the analysis processing unit may determine that the blood vessel extends, and may determine that the blood vessel is newly generated if the travelling directions coincide with each other. In this case, a determined result may be reflected to the blood vessel change data (for example, refer to a right drawing of FIG. 12, a solid line of the right drawing indicates a vascularization part of the blood vessel region, and a broken line thereof indicates an extension part of the blood vessel region). Even when the blood vessel is not present or the travelling direction is not detected in the reference MC image data, the blood vessel may be determined to be vascularization.

Figure 13:
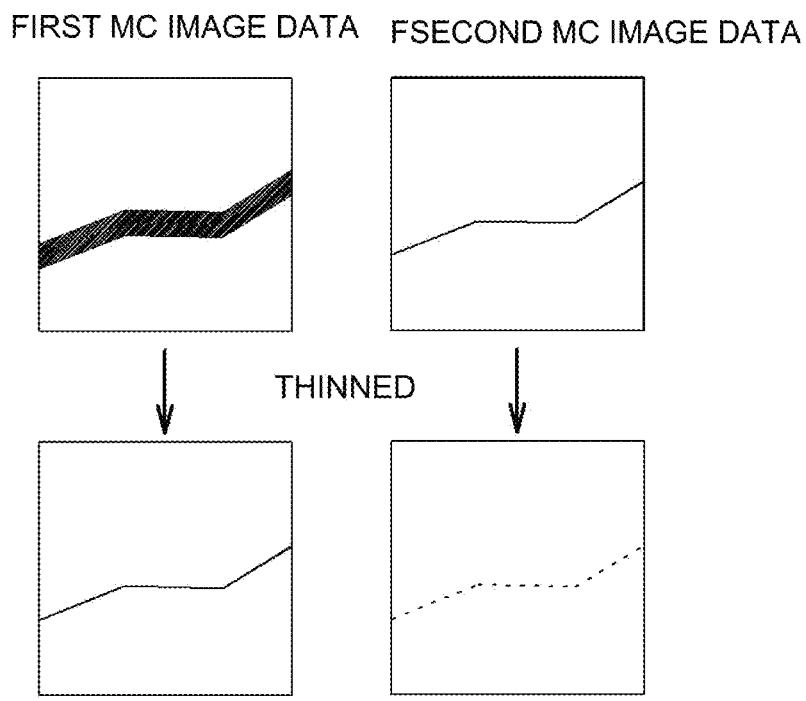
FIG. 13 is a view illustrating an example of a case in which a thinning process is performed on the blood vessel region.
Figure 14:
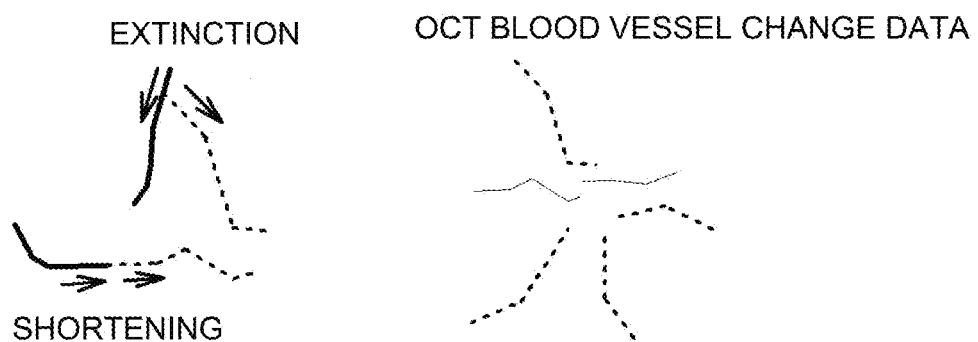
FIG. 14 is a view illustrating an example at the time of determining extinction and shortening of the blood vessel region.

For example, the analysis processing unit may measure a diameter of the blood vessel of the blood vessel region in each MC image data by the image process, and may perform a thinning process with respect to each blood vessel region in each MC image data (for example, refer to FIG. 13). The analysis processing unit may change luminance of a thin line corresponding to each blood vessel region depending on the diameter of the blood vessel. The analysis processing unit may obtain the difference of luminance of each MC image data in which the luminance value is expressed as a thin line having luminance values corresponding to the diameter of the blood vessel. The difference of luminance includes the change of the diameter of the blood vessel. Here, for example, in a case in which the reference MC image data is acquired before the standard MC image data, the blood vessel having a plus difference of luminance may be determined as a blood vessel of which the diameter of the blood vessel expanded, the blood vessel having a minus difference of luminance may be determined as a blood vessel of which the diameter of the blood vessel is decreased, and the blood vessel having zero difference of luminance may be determined as a blood vessel of which the diameter of the blood vessel has not been changed.

The determination of the vascularization and the extension of the blood vessel region and the determination of the expansion of the blood vessel region may be performed by determining presence or absence of a hollow part in the increased region of the blood vessel through the image process, and if the hollow part is present, the blood vessel region is determined to be expanded.

In a case in which the temporal change information in relation to the decrease of the blood vessel region is obtained, for example, based on the first MC image data and the second MC image data, the analysis processing unit may determine whether or not the decrease of the blood vessel region is the extinction (disappearance) of the blood vessel region, the shortening of the blood vessel region, or the cutdown of the blood vessel region. In addition, the analysis processing unit may determine, for example, only one of the extinction of the blood vessel region, the shortening of the blood vessel region, and the expansion of the blood vessel region, and the cutdown of the diameter of the blood vessel or the blood vessel knob.

For example, the analysis processing unit may determine the extinction and the shortening of the blood vessel region by collating the MC image data which is set as the reference image (reference MC image data) with the decreased part of the blood vessel region in the MC image data (standard MC image data) which is set as the standard image. In this case, the collating may be performed in the travelling direction of the blood vessel, and for example, when the travelling direction of a part corresponding to the decreased region (for example, refer to a dotted line of a left drawing of FIG. 14) in the standard MC image data is collated with a travelling direction of the blood vessel (for example, refer to a solid line of a left drawing of FIG. 14) in the reference MC image data, if the travelling directions coincide with each other, the analysis processing unit may determine that the blood vessel is shortened, and if the travelling directions does not coincide with each other, the analysis processing unit may determine that the blood vessel is extinct. In this case, the determined result may be reflected to the blood vessel change data (for example, refer to a right drawing of FIG. 14, a dotted line of the right drawing indicates an extinct part of the blood vessel region, and a thin line indicates a shortened part of the blood vessel region).

The determination of the extinction and the shortening of the blood vessel region and the determination of the cutdown of the blood vessel region may be performed by determining presence and absence of the hollow part in the decreased region of the blood vessel through the image process, and if there is the hollow part, the blood vessel region is cutdown.

<Generation OCT Blood Vessel Change Data in Relation to Blood Vessel Region on Specific Layer>

Figure 15:
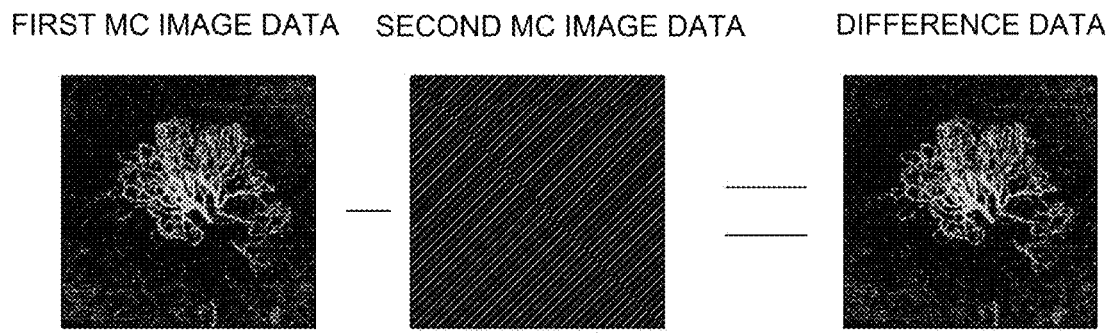
FIG. 15 is a view illustrating an example at the time of obtaining the temporal change in relation to the blood vessel region at a specific layer region.

For example, based on the first MC image data and the second MC image data, the analysis processing unit may generate the OCT blood vessel change data including the temporal change information in relation to the blood vessel region in a specific layer region (for example, refer to FIG. 15).

The specific layer region may be, for example, a layer region including one or a plurality of layers of the fundus or the anterior eye, and the blood vessel region in the specific layer region may be, for example, the blood vessel region in relation to the layer region of a part in the depth direction.

The OCT blood vessel change data in relation to the blood vessel region in the specific layer region may be acquired, for example, based on a difference between the front MC image data items in the specific layer region, or may be acquired based on a difference between the three-dimensional MC image data items in the specific layer region.

As described above, when the OCT blood vessel change data in relation to the blood vessel region on a specific layer is generated, for example, the temporal change in relation to the blood vessel region in the specific layer region can be easily recognized.

The analysis processing unit may respectively generate the OCT blood vessel change data in relation to a plurality of the layer regions, and in this case, the OCT blood vessel change data in relation to each layer region may be imaged and displayed on the display unit. Accordingly, for example, since the temporal change of the blood vessel region in relation to a plurality of the layer regions of the fundus of the subject's eye can be easily recognized, diagnosis can be performed in many directions. The OCT blood vessel change data in relation to the layer region may be displayed with the OCT blood vessel change data in relation to the entire blood vessel region in the depth direction at the same time.

In addition, the analysis processing unit is capable of acquiring the temporal change information in relation to the blood vessel region on a specific layer by obtaining the difference of luminance between the front MC image data items in relation to the specific layer, and is capable of detecting the temporal change of the blood vessel region in the specific layer region as the difference of luminance, even when the blood vessel in the specific layer region is changed in the depth direction.

The front MC image data may be acquired, for example, by calculating three-dimensional MC data (or three-dimensional OCT data) in relation to a specific layer region of a part of the depth direction.

Data in relation to the specific layer region may be acquired, for example, when each data is separated in every layer by performing a segmentation process with respect to the three-dimensional MC data (or, three-dimensional OCT data which becomes basis), or may be acquired by extracting a specific layer.

In a case in which the OCT blood vessel change data in relation to the blood vessel region on the specific layer is obtained, the difference of luminance between the three-dimensional MC image data items may be obtained, and in this case, since the obtained data includes information relating to the depth direction on the specific layer, it is advantageous in that the information including deformation of the blood vessel region in the depth direction can be detected.

In a case in which the OCT blood vessel change data in relation to the blood vessel region on the specific layer is obtained, a segmentation result with respect to at least one of the first MC image data and the second MC image data may be used.

The analysis processing unit may calculate, for example, the OCT blood vessel change data in relation to the blood vessel region in the specific layer region by applying the segmentation result with respect to the MC image data, which is set as a standard image, to the second MC image data which is set as a reference image.

In this case, for example, the analysis processing unit may obtain the standard MC image data in relation to the specific layer from the MC image data, which is set as a standard image, using the segmentation result with respect to the standard MC image data (or OCT image which becomes basis), which is set as a standard image. The analysis processing unit may acquire the object MC image data in relation to the specific layer from object MC image data which is set as an object image using the segmentation result with respect to the standard MC image data. The analysis processing unit may obtain the difference of luminance between the MC image data items in relation to the specific layer which is obtained using the segmentation result of the standard MC image data.

Accordingly, for example, the temporal change of the blood vessel region in relation to the specific layer region can be accurately recognized. Even when the segmentation result is changed due to the temporal change or the like, using the segmentation result of the standard MC image data, the temporal change in relation to the layer region set in the standard MC image data can be accurately recognized.

In addition, when the segmentation result common to the standard MC image data items and the object MC image data items is used, the data items in the same region common to each other can be compared, and the temporal change of the blood vessel region inside the layer region can be precisely measured.

In a case in which the segmentation result of the standard MC image data is reflected, the analysis processing unit may obtain the differences of luminance of the entire MC image data items, and then may acquire the OCT blood vessel change data on the specific layer by applying the segmentation result of the standard MC image data to the difference of luminance of the entire image data.

It is not limited thereto, the segmentation result of the object MC image data may be applied to the standard MC image data.

Of course, it is not limited to the above-described method, the analysis processing unit may acquire the blood vessel change data in relation to the specific layer by applying a segmentation result with respect to the standard MC image data to the standard MC image data, and applying a segmentation result with respect to the reference MC image data to the reference MC image data. In this case, for example, the OCT blood vessel change data including the temporal change information in relation to the entire specific layer region of each MC image data can be acquired by reflecting a difference of the segmentation result to the standard MC image data and the reference MC image data. In this case, each MC image data may be matched with a boundary (front side is a depth side) of one of segmentation result in the depth direction.

<Acquisition of OCT Blood Vessel Change Data in Relation to Outer Layer of Retina>

The analysis processing unit may acquire, for example, the OCT blood vessel change data in relation to an outer layer of retina, based on the difference of luminance between the MC image data items in the outer layer of retina (for example, refer to FIG. 15). Accordingly, for example, temporal change in relation to a newly generated blood vessel in the outer layer of retina can be easily acquired. There are many cases that the newly generated blood vessel of the fundus mainly comes up to the outer layer of retina, the temporal change in relation to increase, decrease, or the like of the newly generated blood vessel can be accurately captured by acquiring the blood vessel change data of the outer layer of retina, and a degree of progress of an ocular disease (for example, age-related macular degeneration) related to the vascularization of the newly generated blood vessel, a treatment result of medication, surgery, or the like can be recognized well.

Incidentally, in FIG. 15, a first MC image data shows a state that a newly generated blood vessel appears in the outer layer of the retina, and a second MC image data shows a state that the newly generated blood vessel disappears from the outer layer of the retina by, for example, medication. Thus, the difference data is almost identical to the first MC image data in FIG. 15.

Regarding the front MC image data in the outer layer of retina, the MC image data (projection artifact) of an inner layer of retina which is expressed as noise in the front MC image in relation to the outer layer of retina may be removed by the image process. In this case, noise in the front MC image in relation to the outer layer of retina may be removed using image data acquired as front MC data in relation to the inner layer of retina.

<Acquisition of OCT Blood Vessel Change Data in Relation to Optic Nerve Fiber Layer of Optic Nerve Head Part>

Based on a difference of luminance between MC image data items relating to a nerve fiber layer of optic nerve head part (hereinafter, optic nerve head part NFL), the analysis processing unit may acquire, for example, OCT blood vessel change data in relation to the optic nerve head part NFL. Accordingly, for example, temporal change in relation to the blood vessel region in the optic nerve head part NFL can be easily acquired. The blood vessel region in the optic nerve head part NFL is highly relevant to glaucoma, and for example, the temporal change in relation to the blood vessel in the optic nerve head part NFL can be accurately captured by acquiring blood vessel change data of the optic nerve head part NFL, and thereby making it possible to well grasping a degree of progress of the glaucoma, a treatment result of medication, surgery, or the like. In this case, the OCT blood vessel change data in relation to only the optic nerve head part NFL may be acquired, or OCT blood vessel change data in relation to a specific layer region (for example, NFL, ganglion cell layer (GCL), or inner plexiform layer (IPL)) including the optic nerve head part NFL may be acquired.

As a first example, for example, the analysis processing unit may generate OCT blood vessel increase-and-decrease data including temporal change information relating to at least one of the increase and the decrease of the blood vessel region of the optic nerve head part NFL in a region inside the optic nerve head part. Accordingly, for example, the increase and the decrease of the blood vessel region in a sieve-shaped plate inside the optic nerve head part can be checked more quantitatively. The sieve-shaped plate is highly likely to be changed depending on progress of the glaucoma, the increase and the decrease of the blood vessel region in the sieve-shaped plate can be recognized, and thus the progress of the glaucoma can be appropriately recognized.

In a case in which the OCT blood vessel change data relating to the optic nerve head part NFL in a region inside the optic nerve head part is obtained, for example, the analysis processing unit may obtain the difference of luminance between the MC image data items, in a state in which a magnification between the MC image data items is corrected so that peripherals of the optic nerve head part between the MC image data items coincide with each other. Accordingly, for example, regardless of change in the size of the optic nerve head part, comparison of the blood vessel regions in the optic nerve head part NFL inside the optic nerve head part is possible. It is not limited to the above-described method, and a difference of luminance between the MC image data items may be calculated in relation to a certain region inside the optic nerve head part centered on the center of the optic nerve head is centered.

As a second example, for example, the analysis processing unit may generate the OCT blood vessel increase-and-decrease data including the temporal change information relating to at least any one of the increase and the decrease of the blood vessel region in the optic nerve head part NFL, in a certain region outside of the optic nerve head part in a region in which the optic nerve head part is removed. Accordingly, for example, in a state of in which the change of the optic nerve head part is removed, the temporal change of the blood vessel region in the optic nerve head part NFL in a vicinity of the optic nerve head part can be checked more quantitatively.

As a third example, for example, the analysis processing unit may generate the OCT blood vessel increase-and-decrease data including the temporal change information relating to at least one of the increase and the decrease of the blood vessel region in the optic nerve head part NFL in a certain region including the optic nerve head part and the outside of the optic nerve head part. Accordingly, for example, the temporal change of the blood vessel region in the optic nerve head part NFL including the optic nerve head part and the vicinity of the optic nerve head part can be recognized.

In a case in which the OCT blood vessel change data in relation to the optic nerve head part NFL is acquired, for example, the MC image data or OCT image data is analyzed by an image process, any one of the optic nerve head part and the vicinity of the optic nerve head part may be specified, or may be specified by manual input of an examiner.

<Acquisition of OCT Blood Vessel Change Data Divided into Each Section>

Figure 5:
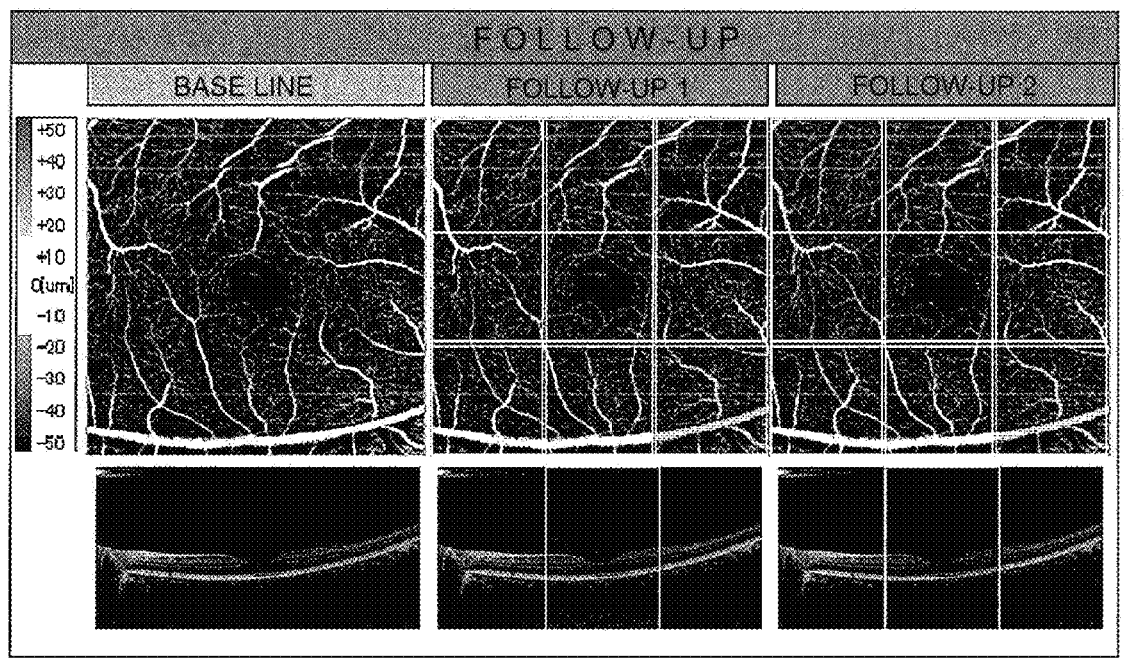
FIG. 5 is a view illustrating an example of the follow-up screen.

The analysis processing unit may generate, for example, OCT blood vessel change data in which the temporal change information in relation to the blood vessel region of the subject's eye is divided into each section as the OCT blood vessel change data (for example, refer to FIG. 5).

The section may be divided, for example, in a grid shape or a chart shape, or may be divided by being focused on a thick blood vessel.

In a case of the chart shape, an analysis chart may be set with respect to blood vessel change image data, or the analysis chart may be, for example, an analysis chart showing an analysis result with respect to data of the difference of luminance in a section, which is set in advance, in each section.

In addition, a disposing position and range of each section in the OCT blood vessel change data may be set to be same as a disposing position and range of each section of the analysis chart set with respect to the OCT data. The analysis chart for the OCT data may be, for example, an analysis chart indicating an analysis result with respect to the OCT data of the section, which is set in advance, in each section.

In a case in which the OCT blood vessel change data divided in each section is obtained, for example, the analysis processing unit may divide the data of the difference of luminance based on the first MC image data and the second MC image data into a plurality of sections. In addition, for example, the analysis processing unit may divide the first MC image data and the second MC image data into the plurality of sections, and may acquire the data of the difference of luminance (for example, a representative value of the difference of the luminance values) in each section.

The analysis processing unit may determine the data of the difference of luminance (for example, a representative value of the difference of the luminance values) in each of the divided sections which are acquired as described above, and may display the temporal change information in relation to the blood vessel region to the display unit in a section unit, based on the determined result in each section. The above-described representative value may be, for example, a total value, an average value, the highest frequency value, or the like, and of course, it is not limited these values.

In a case in which the OCT blood vessel change data divided in each section is displayed on the display unit, for example, the analysis processing unit may display a color map expressed by colors of pixels of the image data depending on the determined result in each section. For example, the analysis processing unit may display a positive section of the difference data as a first color, and a negative section of the difference data as a second color different from the first color. As a display method, it is not limited to the color map, and the analysis processing unit may display the analysis chart in which the determined result in each section based on the difference of luminance becomes an analysis parameter to the display unit as the OCT blood vessel change data.

As described above, when the temporal change information in relation to the blood vessel region is divided in each section, for example, the temporal change information in a section unit within a certain range can be recognized, and it is possible to obtain quantitative data in which variations in each pixel is reduced. In addition, for example, the analysis chart is easily compared with another analysis chart (for example, OCT analysis chart).

<Reflection OCT Blood Vessel Change Data to MC Image Data>

Figure 16:
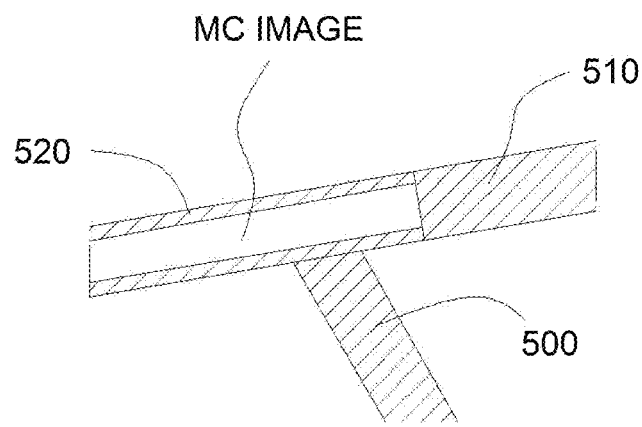
FIG. 16 is a view illustrating an example of a part of the MC image data to which information in relation to increase of the blood vessel region is reflected.
Figure 17:
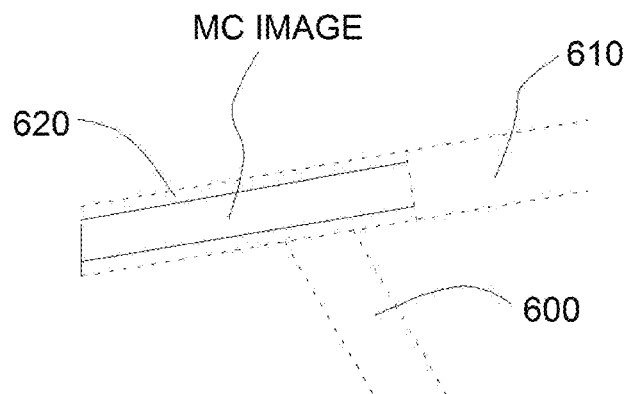
FIG. 17 is a view illustrating an example of a part of the MC image data to which information in relation to decrease of the blood vessel region is reflected.
Figure 18:
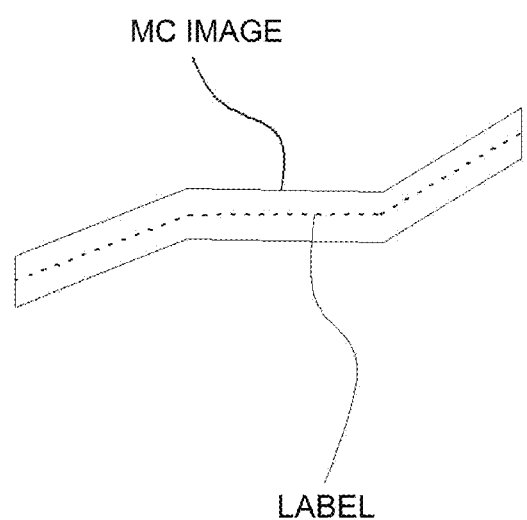
FIG. 18 is a view illustrating an example of a case in which a label in which temporal change information of the blood vessel region is thinned is overlapped with a blood vessel part to be corresponded in the MC image data.

The analysis processing unit may display, for example, image data in which the OCT blood vessel change data is reflected to any one of the first MC image data and the second MC image data to the display unit (for example, refer to FIGS. 16 to 18).

For example, the analysis processing unit may perform an image process with respect to the MC image data based on the OCT blood vessel change data, and may display the MC image data to which the temporal change in relation to the blood vessel region is reflected to the display unit.

For example, the analysis processing unit may overlap the OCT blood vessel change data with the MC image data which is imaged expressed by black and white, and may colorize the MC image data itself based on the temporal change information relating to the OCT blood vessel change data. In addition, the analysis processing unit may attach, for example, a label indicating the temporal change data to the MC image data.

When the OCT blood vessel change data is reflected to the MC image data, for example, the temporal change information relating to the blood vessel change is reflected to the MC image data, and MC image data considering the temporal change is easily diagnosed.

Figure 4:
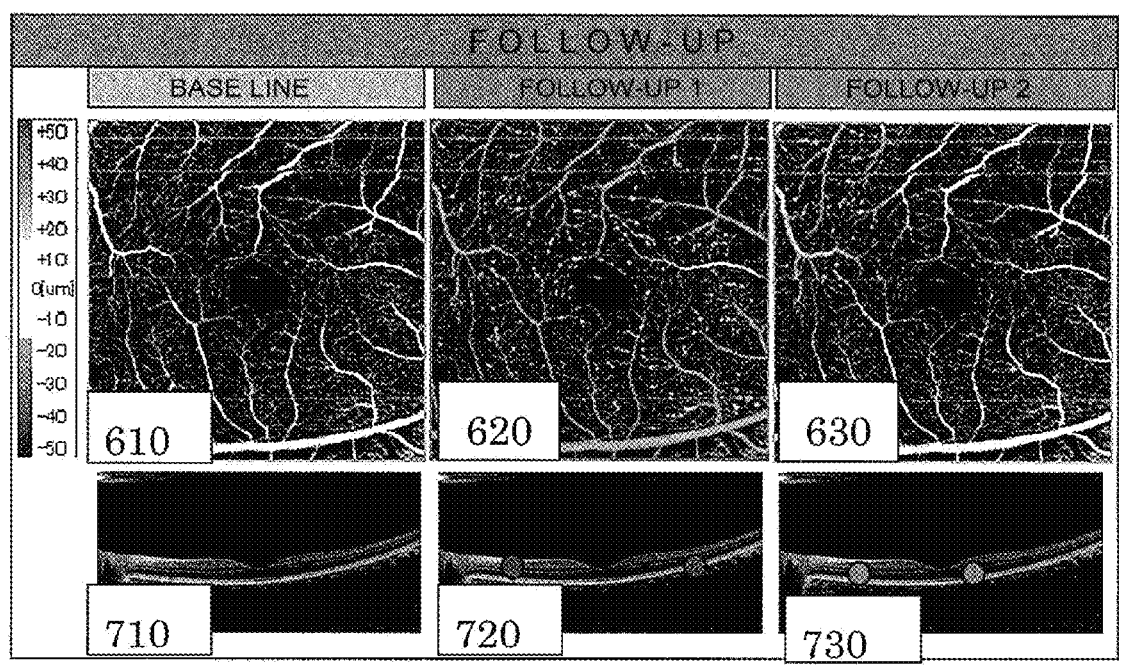
FIG. 4 is a view illustrating an example of a follow-up screen.

The analysis processing unit may perform an image process with respect to the OCT image data based on the OCT blood vessel change data, and may display the OCT image data, to which the temporal change information in relation to the blood vessel region is reflected, to the display unit (for example, refer to OCT image data reference of FIGS. 4 and 5). Accordingly, the temporal change of the blood vessel information relating to an OCT image including morphological information can be checked. In this case, the OCT image data may be B scan OCT image data, may be front OCT image data (en-face OCT image data), or three-dimensional OCT image data.

An example of a part of the MC image data to which information in relation to increase is reflected is illustrated (for example, refer to FIG. 16). In a case of a newly generated blood vessel, the entire newly generated blood vessel in the MC image data may be colorized (for example, blood vessel 500). In addition, in a case of the extension of the blood vessel, a part where the blood vessel in the MC image data extends may be colorized (for example, blood vessel 510). In addition, in a case of the expansion of the diameter of the blood vessel, a part where the diameter of the blood vessel is increased may be colorized (for example, blood vessel 520).

In addition, an example of a part of MC image data to which information in relation to decrease is reflected is illustrated (for example, refer to FIG. 17). In a case of the extinction of the blood vessel, a contour of the entire blood vessel which is extinct may be formed (for example, blood vessel 600). In a case of the shortening of the blood vessel, a contour of a part where the blood vessel in the MC image data is shortened may be displayed (for example, blood vessel 610). In addition, in a case of the cutdown of the diameter of the blood vessel, a contour corresponding to the diameter of the blood vessel in the past with respect to the blood vessel on the MC image data may be displayed (for example, blood vessel 620).

As another example, for example, the analysis processing unit may overlap a label, of which the temporal change information is expressed to be a thin line, with a corresponded blood vessel part in the MC image data (for example, refer to FIG. 18). In this case, the analysis processing unit may change displaying forms of the label depending on contents of the temporal change information. For example, a color of the label may be changed depending on the temporal change information. The label is not limited to change of the color thereof, and a line type of the label may be changed depending on the temporal change information.

For example, in a case in which the temporal change data between the increase and the decrease of the blood vessel region is determined, if the blood vessel region is increased, the label may be expressed by the first color, and if the blood vessel region is decreased, the label may be expressed by the second color different from the first color.

For example, in a case in which the temporal change information among the vascularization, the extension, and the expansion of the blood vessel region is determined, if the blood vessel is newly generated, the label may be expressed by the first color, if the blood vessel extends, the label may be expressed by the second color different from the first color, and if the diameter of the blood vessel expands, the label may be expressed by a third color. In a case in which the temporal change data in relation to the extinction of the blood vessel region, the shortening of the blood vessel, and the cutdown of the diameter of the blood vessel or the blood vessel knob is determined, for example, in the same manner, the labels may be expressed by different colors.

<Acquisition of Analysis Parameter Based on Difference of Luminance Between MC Image Data Items>

The analysis processing unit may acquire, for example, an analysis parameter quantitatively indicating the temporal change in relation to the blood vessel region between the MC image data items based on the difference of luminance. The analysis parameter may be, for example, an analysis parameter (for example, increased area or increased volume) in relation to the increase of the blood vessel region, or an analysis parameter (for example, decreased area or decreased volume) in relation to the decrease of the blood vessel region. In this case, the analysis processing unit may perform, for example, a determination process with respect to the difference of luminance between the MC image data items, and may acquire the analysis parameter based on the determined result. The analysis processing unit may divide, for example, the difference of luminance between the MC image data items into a plurality of sections, and may acquire the analysis parameter in each divided section.

The above-described analysis parameter may be displayed on the display unit, and for example, may be displayed as a graph indicating temporal change, a table type, a color map, or an analysis chart. Of course, a display method is not limited thereto.

<Acquisition of Analysis Result Based on Each MC Image Data>

The analysis processing unit may respectively analyze, for example, the first MC image data and the second MC image data by an image process, may acquire at least one analysis result in relation to each MC image data, and may display the analysis result of each acquired MC image data with the OCT blood vessel change data. Accordingly, since the analysis result based on each MC image data is displayed with the OCT blood vessel change data, the temporal change of the blood vessel region can be checked more accurately.

For example, the analysis processing unit may respectively analyze each MC image data by an image process, may obtain the analysis parameter (for example, blood vessel density, blood vessel area, blood vessel volume, diameter of blood vessel, and meandering degree of blood vessel) in relation to each MC image, and may display the analysis parameter according to each image with the OCT blood vessel change data. The analysis parameter may be expressed as an analysis value (for example, numerical value or grade), may be expressed as each analysis map (for example, blood vessel density map) indicating two-dimensional distribution of the analysis parameter at each position, or an analysis chart indicating a representative value of the analysis parameters according to a plurality of sections. In addition, the analysis parameter may be expressed as a graph indicating the temporal change of analysis values.

In addition, for example, the analysis processing unit may generate the temporal change information relating to the analysis parameter in relation to the blood vessel region obtained in each MC image data, and may display the information on the display unit.

In this case, for example, the analysis processing unit may display a difference map indicating two-dimensional distribution of the difference of the analysis parameter (for example, blood vessel density map) at each position, and may display the analysis chart indicating the difference of the representative value of the analysis parameter in the plurality of sections.

<Follow-Up Based on OCT Image Data and MC Image Data>

For example, the analysis processing unit may respectively analyze each OCT image data acquired at different times by an image process, and may acquire at least one analysis result in relation to each OCT image data.

The analysis processing unit may display the analysis result of each acquired OCT image data with the OCT blood vessel change data. Accordingly, with the OCT blood vessel change data, since the analysis result based on each OCT image data is displayed, it is possible to perform diagnosis in which the temporal change of the blood vessel region and the temporal change of the shape are integrated with each other. The OCT image data may be, for example, OCT image data which becomes basis of the MC image data, or may be OCT image data acquired on the same day (of course, it is not limited thereto).

For example, the analysis processing unit may respectively analyze each OCT image data by an image process, may acquire the analysis parameter (for example, layer thickness, curvature, or size) in relation to each OCT image data, and may display the analysis parameter according to each image with the OCT blood vessel change data.

For example, the analysis processing unit may acquire shape change information indicating the temporal change of the analysis parameter acquired using each OCT image data. The shape change information may be expressed, for example, as a graph indicating change of the analysis value, a difference map indicating a two-dimensional distribution of the difference of the analysis parameter at each position, or the analysis chart indicating the difference of the representative value of the analysis parameter according to a plurality of sections.

In addition, at the time of performing follow-up based on the OCT image data and the MC image data, for example, the analysis processing unit may display each OCT image data acquired at mutually different times and each MC image data acquired at mutually different times to the display unit at the same time. In this case, further, the analysis processing unit may display the OCT blood vessel change data based on each MC image data acquired at mutually different times with each OCT image data and each MC image data at the same time. Accordingly, the temporal change of the blood vessel region can be comprehensively diagnosed with a blood vessel image and a shape image. In this case, when the OCT blood vessel change data in relation to the specific layer region is displayed with the front OCT image data and the front MC image data in relation to the specific layer region, two-dimensional observation in relation to the specific layer region is possible.

<Acquisition of OCT Shape Change Data>

For example, the analysis processing unit may generate OCT shape change data including temporal change information relating to OCT image data in relation to a shape of the subject's eye, based on first OCT image data and second OCT image data of the same subject's eye acquired at mutually different times. The analysis processing unit may generate, for example, the OCT shape change data, based on a difference of luminance between the first OCT image data and the second OCT image data acquired at mutually different times. The difference of luminance may be acquired, for example, according to the acquiring position on the subject's eye (for example, in each pixel or in each section).

Further, the analysis processing unit may display, for example, the OCT shape change data based on the first OCT image data and the second OCT image data acquired at mutually different times and the OCT blood vessel change data based on the first OCTMC image data and the second OCTMC image data acquired at mutually different times on the display unit at the same time. Accordingly, since morphological temporal change and temporal change in relation to the blood vessel region can be observed at the same time, a progress observation in which morphological change and blood vessel result are integrated can be performed.

<Complex Analysis Based on OCT Image Data and MC Image Data>

The analysis processing unit may perform an integration analysis by integrating an analysis result based on the MC image data with an analysis result based on the OCT image data. For example, in a case in which an amount of the increased blood vessel region in relation to the specific layer region is acquired as an analysis parameter based on the temporal change information in relation to the increase and the decrease of the blood vessel region, the analysis processing unit may correct the obtained analysis parameter according to a result of a layer thickness of a specific layer region obtained by the OCT image data. For example, as the resulted layer thickness in the standard MC image data becomes smaller, the analysis parameter may be corrected to become greater, and as the resulted layer thickness in the standard MC image data becomes greater, the analysis parameter may be corrected to become smaller. Accordingly, since the analysis parameter in relation to the amount of the increased blood vessel region can be normalized with respect to a size of the layer thickness, quantitative parameters are obtained.

Modification Embodiment

In the above description, an example of which two MC image data items acquired at different times are compared is described, but it is not limited thereto. For example, the analysis processing unit may acquire the OCT blood vessel change data by comparing three or more MC image data items acquired at mutually different times.

In a case in which three MC image data items acquired at mutually different times are acquired, for example, in a case in which the OCT blood vessel change data is acquired among the first MC image data, the second MC image data acquired later than the first MC image data, and third MC image data acquired later than the second MC image data, the analysis processing unit may obtain, for example, first OCT blood vessel change data based on a difference between the first MC image data and the second MC image data and second OCT blood vessel change data based on a difference between the second MC image data and the third MC image data, and may display these data items on the display unit at the same time.

Since the OCT blood vessel change data items acquired at similar times can be acquired, the temporal change of the blood vessel region can be precisely expressed. In addition, the analysis processing unit may obtain the first OCT blood vessel change data based on the difference between the first MC image data and the second MC image data and the second blood vessel change data based on the difference between the first MC image data and the third MC image data, and may display these data items on the display unit at the same time.

A plurality of the OCT blood vessel change data items are obtained using the common MC image data as a standard. In a case of the above description, the second MC image data or the third MC image data may be used as a standard.

The analysis processing unit may create a time lapse video using at least two OCT blood vessel change data items, and may display the created time lapse video on the display unit.

In the above description, the MC image data items based on the OCT data are compared, but it is not limited thereto, and the analysis processing unit may acquire, for example, the blood vessel change data including the temporal change information in relation to the blood vessel region based on front blood vessel contrast image data acquired using contrast media and the front MC image data based on the three-dimensional OCT data. Even in this case, this exemplary embodiment described above can be applied. The front blood vessel contrast image data may be acquired, for example, by a scanning laser ophthalmoscope (SLO), a fundus camera, or the like.

Accordingly, for example, even when progress observation is performed using, a front blood vessel contrast image using contrast media obtained at the time of a first medical examination and front MC image data obtained later than the first medical examination, the temporal change information in relation to the blood vessel region can be obtained. In a case of the front blood vessel contrast image using the contrast media, a contrast image in a state in which the subject's eye is filled with the contrast media may be used, a contrast image for obtaining difference information may be randomly selected by an examiner, and contrast image data having a high correlation with the front MC image data may be automatically selected.

It is not limited thereto, and even when a difference of luminance between the front blood vessel contrast images using two contrast media acquired at different times is obtained, and blood vessel change information in relation to the blood vessel region is obtained, this exemplary embodiment can be applied.

In the above description, based on the first MC image data and the second MC image data of the subject's eye acquired at mutually different times, a case in which the OCT blood vessel change data of the subject's eye is generated has been described as an example, but it is not limited thereto, and as long as the OCT analysis apparatus is an apparatus for analyzing the OCTMC image data relating to the subject acquired by the OCT apparatus for ophthalmology, the exemplary embodiment and the modification embodiment described above can be applied.

In this case, the analysis processing unit may generate, for example, the OCT blood vessel change data including the temporal change information in relation to the blood vessel region of the subject, based on the first OCTMC image data and the second OCTMC image data relating to the subject acquired at mutually different times. In a case in which the exemplary embodiment and the modification embodiment is applied to the subject, it is needless to say that each item parenthesized by < > described above can be applied.

In addition, regarding disclosed contents of each item parenthesized by < > described above, for example, the contents may be executed in a row in the OCT analysis apparatus, or may be individually executed.

Example

Hereinafter, an ophthalmic analysis apparatus of an example will be described with reference to drawings. Hereinafter, as the ophthalmic analysis apparatus (for example, refer to FIG. 1), the OCT motion contrast data analysis apparatus will be described as an example, an OCT motion contrast data analysis apparatus (hereinafter, OCT analysis apparatus) 1 illustrated in FIG. 1 performs an analysis process on the motion contrast data acquired by an OCT device 10. The OCT motion contrast data includes, for example, the blood vessel information of the subject's eye.

The OCT analysis apparatus 1 is provided with, for example, a controller 70. The controller 70 is realized by, for example, a general CPU (central processing unit) 71, a ROM 72, a RAM 73, and the like. In the ROM 72, for example, an analysis process program for processing the motion contrast data, a program for obtaining the motion contrast data by controlling an operation of the OCT device 10, an initial value, and the like are stored. The RAM 73 temporally stores various information items, for example.

Figure 2:
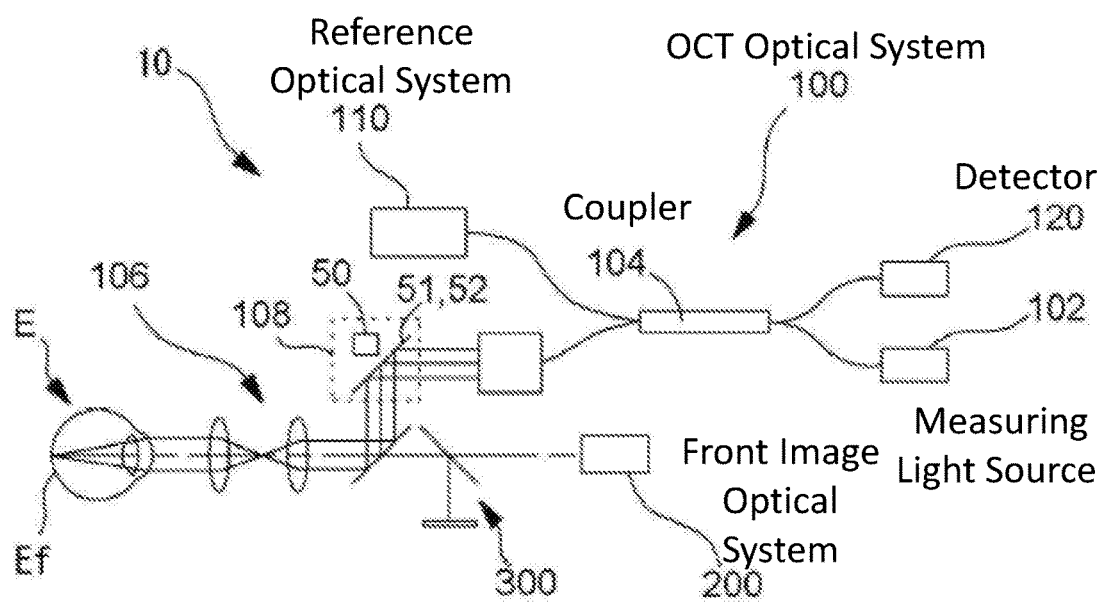
FIG. 2 is a view illustrating an example of an optical system of an OCT device.

In the controller 70, as illustrated in FIG. 1, for example, a storage unit (for example, non-volatile memory) 74, an operating unit 76, a display unit 75, and the like are electrically connected. The storage unit 74 is, for example, a non-transitory storage medium which is capable of holding storage contents even when power supply is blocked. For example, a hard disk drive, the flash ROM, a detachable USB memory, and the like can be used as the storage unit 74.

In the operating unit 76, various operation instructions by the examiner are input. The operating unit 76 outputs a signal in accordance with the input operation instruction to the CPU 71. In the operating unit 76, for example, a user interface of at least one of a mouse, a joystick, a keyboard, a touch panel, and the like may be used.

The display unit 75 may be a display which is mounted on a main body of the OCT analysis apparatus 1, and may be a display which is connected to the main body. For example, a display of a personal computer (hereinafter, refer to "PC") may be used. The display unit 75 displays, for example, the OCT data acquired by the OCT device 10, the motion contrast data, and the like.

For example, the OCT device 10 is connected to the OCT analysis apparatus 1 of the example. The OCT analysis apparatus 1 may be integrally configured with a case same as, for example, the OCT device 10, or may be separately configured. The controller 70 may acquire the motion contrast data from the connected OCT device 10. The controller 70 may acquire the motion contrast data acquired by the OCT device 10 through a storage medium.

<OCT Device>

Hereinafter, an outline of the OCT device 10 will be described on the basis of FIG. 2. For example, the OCT device 10 applies measuring light to a subject's eye E, and acquires an OCT signal acquired by reflecting light and the measuring light. The OCT device 10 is mainly provided with, for example, an OCT optical system 100.

<OCT Optical System>

The OCT optical system 100 applies the measuring light to the subject's eye E, and detects an interference signal of the reflecting light and reference light. The OCT optical system 100 is mainly provided with, for example, a measuring light source 102, a coupler (optical splitter) 104, a measurement optical system 106, a reference optical system 110, a detector 120, and the like. Regarding a detailed configuration of the OCT optical system, for example, refer to JP-A-2015-131107.

The OCT optical system 100 is an optical system of a so called optical coherence tomography (OCT). The OCT optical system 100 divides light emitted from the measuring light source 102 into the measuring light (sample light) and the reference light by the coupler 104. The measuring light is guided to the measurement optical system 106, and the reference light is guided to the reference optical system 110. The measuring light is guided to a fundus Ef of the subject's eye E through the measurement optical system 106. After that, the detector 120 receives the interference light by combining the measuring light reflected by the subject's eye E and the reference light.

The measurement optical system 106 is provided with, for example, a scanning unit (for example, light scanner) 108. The scanning unit 108 may be provided, for example, for scanning the measuring light in an XY direction on the fundus (transverse direction). For example, the CPU 71 controls an operation of the scanning unit 108 based on scan position information which is set, and acquires the OCT signal based on a light receiving signal detected by the detector 120. The reference optical system 110 generates the reference light which is combined with a reflecting light acquired by reflection of the measuring light in the fundus Ef. The reference optical system 110 may be Michelson type or Mach-Zehnder type.

The detector 120 detects an interference state of the measuring light and the reference light. In a case of Fourier domain OCT, a spectral intensity of the interference light is detected by the detector 120, and a depth profile (A scan signal) in a predetermined range by Fourier transform with respect to spectral intensity data is acquired.

As the OCT device 10, for example, Spectral-domain OCT (SD-OCT), Swept-source OCT (SS-OCT), Time-domain OCT (TD-OCT), and the like may be used.

<Front Imaging Optical System>

The front imaging optical system 200 images, for example, the fundus Ef of the subject's eye E in a front direction (for example, optical axis direction of measuring light), and obtains a front image of the fundus Ef. The front imaging optical system 200 may be, for example, an apparatus configuration of a scanning type laser ophthalmoscope (SLO) (for example, refer to JP-A-2015-66242), and may be a so called fundus camera type configuration (refer to JP-A-2011-10944). As the front imaging optical system 200, the OCT optical system 100 may be also used with, and the front image may be acquired on the basis of a detecting signal from the detector 120.

<Fixation Target Projecting Unit>

A fixation target projecting unit 300 includes the optical system for guiding a gaze direction of an eye E. The fixation target projecting unit 300 includes a fixation target being presented on the eye E, and is capable of guiding the eye E. For example, the fixation target projecting unit 300 has a visible light source which emits visible light, and changes a presentation position of the fixation target in two-dimension. Thus, the gaze direction is changed, and consequently, an acquiring part of the OCT data is changed.

<Acquisition of Motion Contrast Data>

Figure 3A:
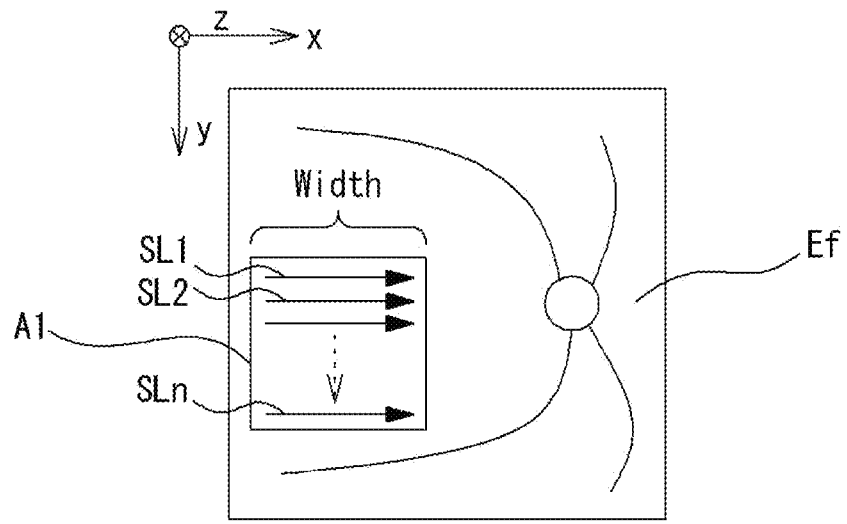
FIGS. 3A, 3B, and 3C are views for describing an example of acquisition of motion contrast.

The OCT analysis apparatus 1 of the example may acquire the motion contrast data, for example, by processing the OCT data detected by the OCT device 10. The CPU 71 controls driving of the scanning unit 108, and applies the measuring light to a region A1 on the fundus Ef. In FIG. 3A, a direction of a z axis is set to a direction of an optical axis of the measuring light. A direction of an x axis is set to a horizontal direction of an examinee perpendicular to the z axis. A direction of a y axis is set to a vertical direction of the examinee perpendicular to the z axis.

For example, the CPU 71 applies the measuring light in an x direction along scan lines SL1, SL2, . . . , and SLn in a region A1. Scanning in a direction intersecting with an optical direction of the measuring light (for example, x direction) with the measuring light is referred to as "B scan". Two-dimensional OCT data obtained by one time B scan will be described as two-dimensional OCT data of one frame. The CPU 71 may obtain an A scan signal of a z direction in each scanning position by applying the measuring light to, for example, an xy direction in two-dimension.

The CPU 71 may acquire the motion contrast data based on the OCT data. The motion contrast may be, for example, information capturing a blood flow of the subject's eye, a change of a retinal tissue, and the like. In a case of acquiring the motion contrast data, the CPU 71 acquires at least two OCT data of the subject's eye in relation to a same position at different timings. For example, in each the scan line, the CPU 71 performs the B scan in multiple times at different timings, and respectively acquires a plurality of the OCT data items at different timings.

Figure 3B:
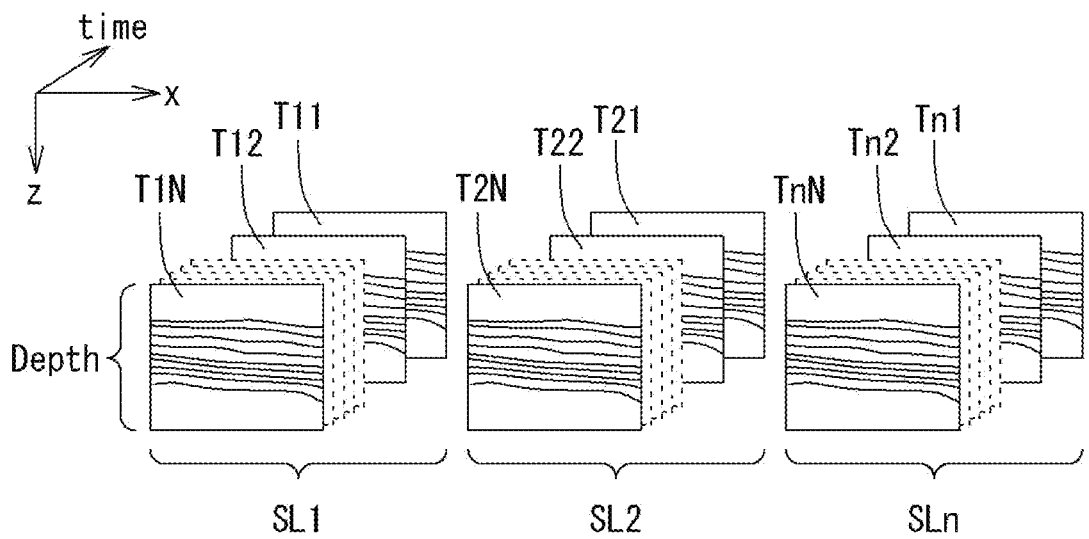
Figure 3C:
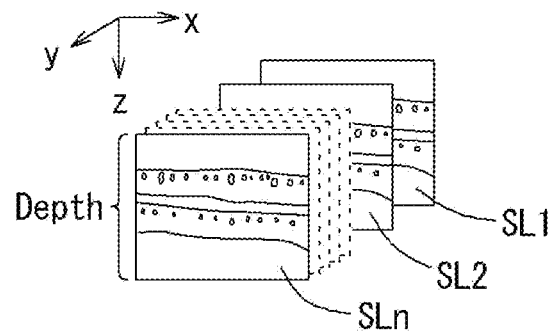

For example, FIG. 3B illustrates the OCT signal acquired in a case in which the B scan is performed in multiple times at different timings in the scan lines SL1, SL2, . . . , and SLn. For example, FIG. 3B illustrates a case of applying the scan line SL1 at timings T11, T12, . . . , and T1N, applying the scan line SL2 at timing T21, T22, . . . , and T2N, and applying the scan line SLn at timings Tn1, Tn2, . . . , and TnN. For example, the CPU 71 acquires the plurality of OCT data items at different timings in each the scan line, and stores the OCT data to the storage unit 74.

As described above, if the plurality of OCT data items in relation to the same position at the different timings are acquired, the CPU 71 acquires the motion contrast data by processing the OCT data. As a calculating method of the OCT data for acquiring the motion contrast, for example, a method of calculating an intensity difference or an amplitude difference of complex OCT data, a method of calculating dispersion of intensity or amplitude or standard deviation of the complex OCT data (Speckle variance), a method of calculating a phase difference or dispersion of the complex OCT data, a method of calculating a vector difference of the complex OCT data, a method of multiplying the phase difference and the vector difference of a complex OCT signal, and the like are exemplified. As an example of a calculating method, for example, refer to JP-A-2015-131107.

The CPU 71 may acquire three-dimensional motion contrast data of the subject's eye E by arranging the motion contrast data in different scan lines. As described above, as the motion contrast data, the intensity difference, the vector difference, and the like may be acquired without being limited to the phase difference.

Hereinafter, operations of the devices according to the example described above will be described. When a follow-up analysis mode for performing a follow-up analysis in relation to the MC image data is set, the CPU 71 may read at least two MC image data items acquired at different times from the storage unit 74, and may display the read data on the display unit 75 as a follow-up screen.

Figure 6:
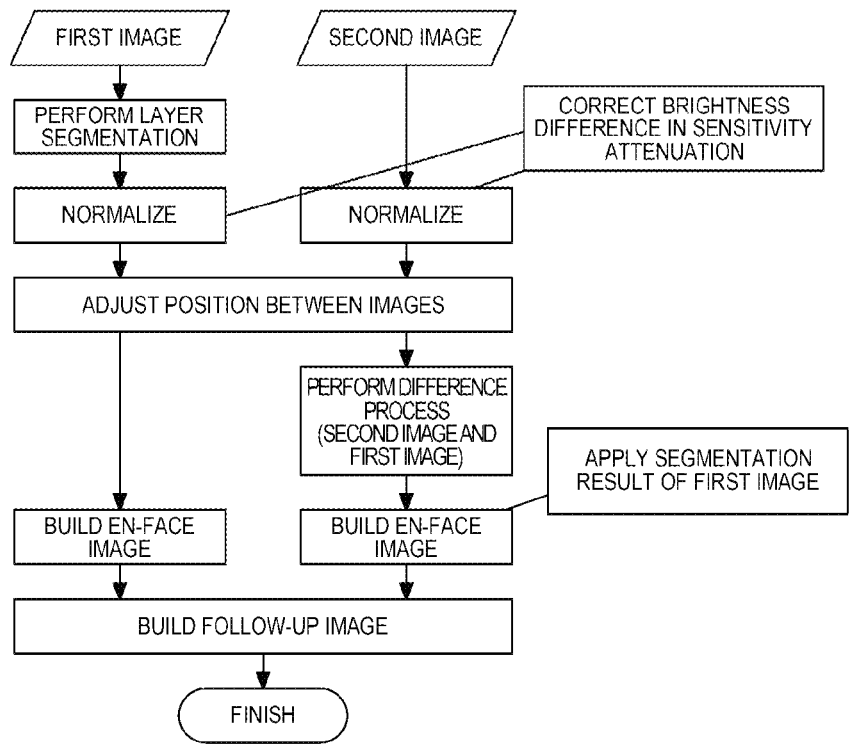
FIG. 6 is a view illustrating an example of an analysis process for acquiring temporal change.
Figure 7:
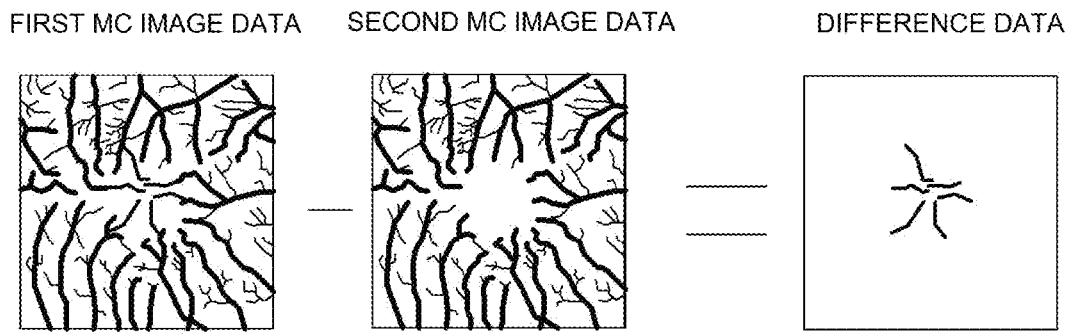
FIG. 7 is a view illustrating an example at the time of obtaining a difference of luminance.
Figure 8:
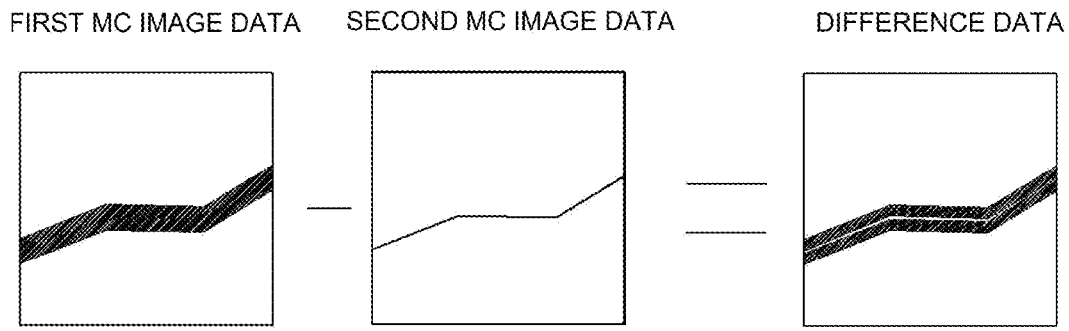
FIG. 8 is a view illustrating an example at the time of obtaining the difference of luminance.

FIG. 6 is a flow chart for describing a process flow for building the follow-up screen according to the example. Here, the first MC image and the second MC image are MC image acquired on mutually different examination dates.

In the first MC image, a segmentation process for dividing the first MC image into each layer or extracting the specific layer may be performed. The process may be executed at the time of building the front MC image in relation to the specific layer.

Next, in order to correct a brightness difference between the MC images due to the influence of the sensitivity attenuation in the depth direction, a normalizing process may be executed on the first MC image and the second MC image. In addition, in a case in which the sensitivity attenuation is small (in a case in which a position of each MC image in the depth direction in the image is not changed, an apparatus (for example, SS-OCT) having originally small sensitivity attenuation is used and the like), the normalizing process may be omitted.

Various types of methods for image normalization are considered, but for example, a coefficient of change of the luminance in the depth direction is obtained in advance, and then the obtained MC image may be multiplied by the coefficient, or contrast adjustment (histogram flattening or the like) between the MC images may be executed. In addition, a method of correcting differences so that luminance of the same part coincides with another after performing the position adjustment between the MC images may be used.

In order to correct a position deviation between the MC images, at least a position adjusting process in the depth direction may be performed between the first MC image and the second MC image. Position adjustment between images (XY direction) in a plane direction may be omitted if tracking photography or the like is executed. The normalizing process and the position adjustment may be performed in a reverse order.

After the normalizing process and the position adjustment are performed, a difference process of obtaining a difference of luminance between the first MC image and the second MC image may be performed.

Next, the front MC image relating to the specific layer may be built in relation to each MC image. In this case, the change is easily captured by applying the segmentation result of the first MC image to the second MC image. In this case, the segmentation result of the first MC image may be used for being applied to the second MC image as it is, or segmentation of the second MC image may be performed again using the segmentation result of the first MC image as reference data, and the second MC image may be set to be positioned on the original layer. At the time of performing layer-segmentation of the first MC image, layer division may be performed using the blood vessel information relating to the MC image.

After that, the follow-up screen is built, and the follow-up screen is displayed on the display unit. In the follow-up screen, for example, each front MC image, the OCT blood vessel change data based on the difference process, and the like are displayed.

In the above-described example, the OCT blood vessel change data is obtained by executing the difference process with respect to the MC image itself, but for example, after a frame of the blood vessel is detected by performing the thinning process on the MC image, the difference process is executed between the MC images, and thus the OCT blood vessel change data may be obtained. Accordingly, noise other than the blood vessel change is removed, and presence and absence of the blood vessel can be easily analyzed.

FIG. 4 is a view illustrating an example of the follow-up screen. The follow-up screen includes MC image (standard image) 610 of a base line corresponding to the first MC image, MC images 620 and 630 (reference image) of follow-up corresponding to the second MC image, and OCT images 710 to 730 corresponding to each MC image. The MC image 610 is compared with the MC images 620 and 630 as an image of the base line. The MC images 620 and 630 of the follow-up are images captured on an examination date later than the MC image 610, and are standardized to the MC image 610. The MC image 630 of the follow-up is an image captured on an examination date later than the MC image 620.

The CPU 71 obtains a difference of luminance of the MC images 620 and 630 based on the MC image 610 as a standard image, and the OCT blood vessel change data is obtained based on the obtained difference. Here, the CPU 71 acquires the OCT blood vessel change data in relation to the vascularization and the extinction of the blood vessel region, and overlaps the acquired OCT blood vessel change data with the MC images 620 and 630. In this case, the increased part and the decreased part in the blood vessel region may be displayed with different colors. In FIG. 4, the images are colorized in each pixel according to the blood vessel change information.

The MC image 620 is an example in which the blood vessel region (blood vessel and blood vessel knob) is extinct when compared with the MC image 610, and the extinct part of the blood vessel region may be highlighted in the first color (for example, blue) so as to be displayed in the MC image 620. The MC image 630 is an example in which the blood vessel region (blood vessel and blood vessel knob) is newly generated when compared with the MC image 610, in the MC image 630, and the vascularization part of the blood vessel region may be highlighted in the second color (for example, red) different from the first color so as to be displayed. Because of the display, since the changed part of the blood vessel region can be checked in the MC image, diagnosis in consideration of the changed part can be easily performed.

In addition, in the OCT image 720, the extinct part of the blood vessel corresponding to the highlighted and displayed part of the MC image 620 may be highlighted and displayed. In addition, in the OCT image 730, the vascularization part of the blood vessel corresponding to the highlighted and displayed part of the MC image 630 may be highlighted and displayed. Because of the display, since the changed part of the blood vessel region can be checked in the OCT image, diagnosis in consideration of the changed part can be easily performed.

In the above description, as the MC image of the base line, the MC images 620 and 630 captured on the examination date later than the MC image 610 may be set.

In the example described above, the changed part in the MC image is colored, but it is not limited thereto, and the colored changed part may be displayed without the MC image. Accordingly, the changed part can be more highlighted. In a case of colorizing, grayscale may be performed on the changed part according to the magnitude of the difference of the luminance value. Accordingly, the change can be captured without distinguishing the vascularization and the extinction.

In the above description, colorizing is performed in each pixel, but the MC image is divided into a plurality of regions, and each of the divided region may be colored (refer to FIG. 5). In this case, the OCT image is divided according to the division of the MC image, and color-coding in relation to the increase and the decrease of the blood vessel may be performed.

The divided region may be formed in a grid shape or a chart shape (for example, a chart may be used as long as positional association of ETDRS and GCHART for analyzing the OCT image is possible), and may be each region where a thick blood vessel dominates.

What is claimed is:

1. An ophthalmic analysis method comprising:
acquiring first optical coherence tomography (OCT) MC (motion contrast) image data of a subject's eye and second OCT MC image data of the subject's eye using at least one OCT apparatus for ophthalmology, the first OCT MC image data and the second OCT MC image data being acquired at different times;
analyzing the acquired first OCT MC image data and second OCT MC image data to generate OCT blood vessel change data including temporal change information in relation to a blood vessel region of the subject's eye based on the first OCT MC image data and the second OCT MC image data; and
wherein, as the OCT blood vessel change data, OCT blood vessel increase-and-decrease data which includes temporal change information in relation to at least one of increase-and-decrease of a blood vessel region of the subject's eye is generated based on the first OCT MC image data and the second OCT MC image data.

2. The ophthalmic analysis method according to claim 1, wherein
a position adjusting process is performed to adjust a position of the first OCT MC image data and a position of the second OCT MC image data in a depth direction, and
the OCT blood vessel change data is generated based on the first OCT MC image data and the second OCT MC image data on which the position adjusting process is performed.

3. The ophthalmic analysis method according to claim 1, wherein corrects a brightness difference between the first OCT MC image data and the second OCT MC image caused by an influence of sensitivity attenuation in the depth direction is corrected.

4. An ophthalmic analysis method comprising:
acquiring first optical coherence tomography (OCT) MC (motion contrast) image data of a subject's eye and second OCT MC image data of the subject's eye using at least one OCT apparatus for ophthalmology, the first OCT MC image data and the second OCT MC image data being acquired at different times;
analyzing the acquired first OCT MC image data and second OCT MC image data to generate OCT blood vessel change data including temporal change information in relation to a blood vessel region of the subject's eye based on the first OCT MC image data and the second OCT MC image data; and
wherein OCT blood vessel increase-and-decrease data which includes the temporal change information in relation to the increase and the decrease of the blood vessel region of the subject's eye is generated based on the first OCT MC image data and the second OCT MC image data, and is displayed on a display unit in such a manner that increase of blood vessel region is different from the decrease of the blood vessel region in displaying forms.

5. The ophthalmic analysis method according to claim 1, wherein the OCT blood vessel increase-and-decrease data includes the temporal change information in relation to at least one of vascularization and extinction of the blood vessel region of the subject's eye.

6. The ophthalmic analysis method according to claim 1, wherein a segmentation result with respect to the first OCT MC image data is applied to the second OCT MC image data, and the OCT blood vessel change data in relation to a specific layer region is obtained.

7. The ophthalmic analysis method according to claim 1, wherein in the OCT blood vessel change data, temporal change in relation to the blood vessel region of the subject's eye is divided in each section.

8. The ophthalmic analysis method according to claim 1, wherein the OCT blood vessel change data includes the temporal change information in relation to the blood vessel region of the subject's eye in the specific layer region.

9. The ophthalmic analysis method according to claim 1, wherein
the analysis the first OCT MC image data and the second OCT MC image data are analyzed by an image process to acquire at least one of analysis parameters in relation to the first OCT MC image data and the second OCT MC image data, and
at least one of the analysis parameters is displayed with the OCT blood vessel change data.

10. The ophthalmic analysis method according to claim 1, wherein image data in which the OCT blood vessel change data is reflected to any one of the first OCT MC image data and the second OCT MC image data is displayed on a display unit.

11. The ophthalmic analysis method according to claim 1, wherein the OCT blood vessel change data is generated based on a difference of luminance between first MC image data and second MC image data.

12. The ophthalmic analysis method according to claim 1, wherein the first OCT MC image data and the second OCT MC image data acquired at different times are OCT MC image data of a fundus of the subject's eye.

13. An ophthalmic analysis apparatus comprising:
a processor; and
memory storing computer readable program, when executed by the processor, causing the ophthalmic analysis apparatus to execute:
acquiring first optical coherence tomography (OCT) MC (motion contrast) image data of a subject's eye and second OCT MC image data of the subject's eye using at least one OCT apparatus for ophthalmology, the first OCT MC image data and the second OCT MC image data being acquired at different times;

analyzing the acquired first OCT MC image data and second OCT MC image data to generate OCT blood vessel change data including temporal change information in relation to a blood vessel region of the subject's eye based on the first OCT MC image data and the second OCT MC image data; and wherein, as the OCT blood vessel change data, OCT blood vessel increase-and-decrease data which includes temporal change information in relation to at least one of increase-and-decrease of a blood vessel region of the subject's eye is generated based on the first OCT MC image data and the second OCT MC image data.

14. A non-transitory computer readable recording medium storing a computer readable program, when executed by a processor of an ophthalmic analysis apparatus, causing the ophthalmic analysis apparatus to execute:

acquiring first optical coherence tomography (OCT) MC (motion contrast) image data of a subject's eye and second OCT MC image data of the subject's eye using at least one OCT apparatus for ophthalmology, the first OCT MC image data and the second OCT MC image data being acquired at different times;

analyzing the acquired first OCT MC image data and second OCT MC image data to generate OCT blood vessel change data including temporal change information in relation to a blood vessel region of the subject's eye based on the first OCT MC image data and the second OCT MC image data; and wherein, as the OCT blood vessel change data, OCT blood vessel increase-and-decrease data which includes temporal change information in relation to at least one of increase-and-decrease of a blood vessel region of the subject's eye is generated based on the first OCT MC image data and the second OCT MC image data.

\* \* \* \* \*